United States Patent
Rowlen et al.

(10) Patent No.: US 9,850,979 B2
(45) Date of Patent: Dec. 26, 2017

(54) FLOW CYTOMETER WITH OPTICAL SYSTEM ASSEMBLY HAVING VIBRATION ISOLATION AND SHEAR PROTECTION STRUCTURES

(71) Applicant: IntelliCyt Corporation, Albuquerque, NM (US)

(72) Inventors: Kathy L. Rowlen, Longmont, CO (US); Erica Dawson Tenent, Broomfield, CO (US); Garrett S. Wilson, Erie, CO (US); Christopher H. Converse, Boulder, CO (US)

(73) Assignee: IntelliCyt Corporation, Albuquerque, NM (US)

( * ) Notice: Subject to any disclaimer, the term of this patent is extended or adjusted under 35 U.S.C. 154(b) by 0 days.

(21) Appl. No.: 15/316,093

(22) PCT Filed: Jun. 2, 2015

(86) PCT No.: PCT/US2015/033795
§ 371 (c)(1),
(2) Date: Dec. 2, 2016

(87) PCT Pub. No.: WO2015/187700
PCT Pub. Date: Dec. 10, 2015

(65) Prior Publication Data
US 2017/0198782 A1    Jul. 13, 2017

Related U.S. Application Data

(60) Provisional application No. 62/008,401, filed on Jun. 5, 2014.

(51) Int. Cl.
*G01N 15/14*    (2006.01)
*F16F 15/08*    (2006.01)
(Continued)

(52) U.S. Cl.
CPC ......... *F16F 15/08* (2013.01); *G01N 15/1436* (2013.01); *G01N 15/1459* (2013.01);
(Continued)

(58) Field of Classification Search
CPC .......................................................... G01L 5/14
(Continued)

(56) References Cited

U.S. PATENT DOCUMENTS 3,516,629 A    6/1970    Say
3,758,058 A    9/1973    Neudeck et al.
(Continued)

FOREIGN PATENT DOCUMENTS

EP    0822404 A2    2/1998
EP    1002968 A2    5/2000
(Continued)

*Primary Examiner* — Arlen Soderquist
(74) *Attorney, Agent, or Firm* — Marsh Fischmann & Breyfogle LLP

(57) ABSTRACT

A flow cytometer may include a vibration isolation structure on which a flow cytometer optical system assembly is supported when the flow cytometer is in an operational configuration. A shear protection structure may be positioned to protect a vibration isolation structure from damage during handling and shipping. A flow cytometer optical system assembly may include optical component units fixed in position on a support platform with adjustability of one or more optical features in the optical component units. A light-tight dichroic mirror unit may include a rotatably mounted dichroic mirror with a locking mechanism to permit re-setting angular positioning of a dichroic mirror.

20 Claims, 19 Drawing Sheets

(51) Int. Cl.
G01N 15/00 (2006.01)
G01N 15/10 (2006.01)

(52) U.S. Cl.
CPC  F16F 2224/025 (2013.01); G01N 2015/0065 (2013.01); G01N 2015/1006 (2013.01)

(58) Field of Classification Search
USPC .................................. 422/73, 82.05; 436/63
See application file for complete search history.

(56) References Cited

U.S. PATENT DOCUMENTS

| | | | |
|---|---|---|---|
| 4,007,612 A * | 2/1977 | Brimer | D06F 37/206 |
| | | | 210/363 |
| 4,076,420 A * | 2/1978 | De Maeyer | G01N 21/253 |
| | | | 356/246 |
| 4,857,451 A | 8/1989 | Schwartz | |
| 5,386,962 A | 2/1995 | Adriance et al. | |
| 5,641,457 A * | 6/1997 | Vardanega | B01L 1/04 |
| | | | 250/461.2 |
| 5,736,105 A | 4/1998 | Astle | |
| 6,421,479 B1 * | 7/2002 | Harr | G02B 6/29314 |
| | | | 385/10 |
| 8,482,731 B2 | 7/2013 | Muraki | |
| 2002/0185604 A1 * | 12/2002 | Coates | G01N 21/031 |
| | | | 250/339.07 |
| 2003/0235919 A1 | 12/2003 | Chandler | |
| 2006/0038989 A1 | 2/2006 | Domack | |
| 2006/0244943 A1 * | 11/2006 | Opower | G03F 7/70391 |
| | | | 355/72 |
| 2010/0220315 A1 * | 9/2010 | Morrell | G01N 15/1436 |
| | | | 356/73 |
| 2012/0070818 A1 | 3/2012 | Rowlen | |
| 2012/0217914 A1 | 8/2012 | Mawhinney | |
| 2013/0050782 A1 | 2/2013 | Heng | |
| 2013/0080082 A1 | 3/2013 | Howes | |
| 2013/0327957 A1 | 12/2013 | Ayliffe | |
| 2015/0277236 A1 * | 10/2015 | Sato | G03F 7/70341 |
| | | | 355/30 |
| 2017/0115203 A1 * | 4/2017 | Smolak | G01N 15/1436 |
| 2017/0138835 A1 * | 5/2017 | Wilson | G01N 15/1404 |
| 2017/0205331 A1 * | 7/2017 | Smolak | G01N 15/1429 |

FOREIGN PATENT DOCUMENTS

| | | |
|---|---|---|
| EP | 1176412 A2 | 1/2002 |
| WO | 2008010120 A2 | 1/2008 |
| WO | 2009093017 A1 | 7/2009 |

* cited by examiner

FLOW CYTOMETER WITH OPTICAL SYSTEM ASSEMBLY HAVING VIBRATION ISOLATION AND SHEAR PROTECTION STRUCTURES

CROSS-REFERENCE TO OTHER APPLICATIONS

This application is related to a concurrently filed international patent application under the Patent Cooperation Treaty entitled "AUTOMATED ALIGNMENT OF OPTICS WITHIN A FLOW CYTOMETER" filed with the U.S. Patent and Trademark Office as receiving office, assigned international application number PCT/US15/33803 and this application is related to U.S. provisional patent application Ser. No. 62/008,371 entitled "AUTOMATED ALIGNMENT OF OPTICS WITHIN A FLOW CYTOMETER" filed Jun. 5, 2014, the entire contents of each such referenced application being incorporated herein by reference. This application claims the benefit of U.S. provisional application Ser. No. 62/008,401 entitled "FLOW CYTOMETER WITH OPTICAL SYSTEM ASSEMBLY" filed Jun. 5, 2014, the entire contents of which are incorporated herein by reference.

FIELD OF THE INVENTION

This disclosure relates to flow cytometry, including flow cytometry devices and related methods.

BACKGROUND OF THE INVENTION

Flow cytometry is an analytical technique used in a number of applications to measure physical and/or chemical properties of biological or non-biological particles as they flow in a sample fluid through an investigation cell, commonly referred to as a flow cell. Although the sample fluid may be investigated by subjecting the sample fluid to a variety of stimuli, light is one common stimulus technique. Scattered light exiting from the flow cell may be detected and analyzed to provide information on the characteristics of particles present in the sample fluid. Light stimulation and light detection techniques may be tailored to identification of particular characteristics indicative of the presence of particular types of particles. For example, one technique is to stain a sample fluid with one or more stains (also referred to as dyes) that associate with a particular biological component of interest. The stains may have fluorescent activity that provides a fluorescent emission in a particular wavelength range, the detection of which provides an indication of the presence of that biological component. For example, two different fluorescent stains, one that associates with protein and another that associates with nucleic acid, may aid in the detection of virus particles. Light detection may be designed to specifically detect light at the different fluorescent emission wavelengths of different stains. This may involve splitting light received from the flow cell into different light wavelength ranges, such as using a dichroic mirror that passes some wavelengths of light while reflecting other wavelengths of light.

Devices for performing flow cytometry are referred to as flow cytometers. Flow cytometers are often designed to optimize detection of a specific type of particle, for example specific cells, bacteria or virus. A complicating issue for flow cytometer robustness and durability over a prolonged period is that flow cytometers tend to be very sensitive instruments that require very precise alignment of optical elements for optimal performance. Flow cytometry optical elements, which may include a light source, a flow cell, lenses, beam splitters and light detectors, are typically precisely located and secured in place in the flow cytometer with a desired alignment within and protected by a protective enclosure, or shell. To provide some ability to fine-tune alignment of the delivery of light to the flow cell, a light source, such as a laser, may be mounted on an adjustable mount that permits some adjustment of the positioning and orientation of the light source to permit some fine-tuning of the alignment with the flow cell or with a lens disposed between the light source and the flow cell.

Even with optical components firmly secured in place, flow cytometers are susceptible to significant performance degradation during operation from even slight physical environment disturbances such as ambient vibrations, including incidental bumps or mechanical shocks, and are susceptible to significant loss of performance over time from even slight changes in the alignment of optical elements that may occur over a prolonged period. These performance degradations may be even more problematic for flow cytometers that are operated to detect extremely small particles, such as virus particles. Maintaining a high level of performance may involve frequent and expensive servicing of a flow cytometer. In addition, significant degradation of optical element alignment and damage to fragile equipment may occur during shipping and handling operations, which may limit the range of equipment that may practically be used and/or may require significant servicing of the flow cytometer on-site after shipping and prior to use.

SUMMARY OF THE INVENTION

Various aspects this disclosure are directed to flow cytometers that include:
a light source unit including a light source;
a flow cell unit comprising a flow cell with an investigatory flow path to conduct sample fluid flow through the flow cell during operation of the flow cytometer to perform a flow cytometry investigation of sample fluid in the flow cell;
a first optical path between the light source and the flow cell to direct light from the light source to at least a portion of the investigatory flow path;
a light detection system including at least one light detector; and
a second optical path between the investigatory flow path and the light detection system to direct at least a portion of light from the investigatory flow path to the light detection system.

In a first aspect, a flow cytometer may include a vibration isolation structure and a flow cytometry optical system assembly disposed in an enclosure. The flow cytometry optical system assembly may comprise a support platform and flow cytometry optical components supported by the support platform, with the flow cytometry optical components comprising the light source unit, the flow cell unit and the light detector. The flow cytometer may have an operational configuration in which the flow cytometry optical system assembly within the enclosure is supported by the vibration isolation structure to provide a barrier to propagation of vibrations to the flow cytometry optical system assembly.

In a second aspect, a flow cytometer may have a mirror unit including a mirror disposed along the first optical path between the light source and the flow cell, with the mirror disposed to reflect light from the light source along the first optical path toward the investigatory flow path of the flow cell. The flow cytometer may have a flow cytometry optical system assembly as per the first aspect, with the flow cytometry optical components supported on a support platform including the mirror unit, and with the mirror being adjustable within the mirror unit to adjust orientation of the mirror, for example relative to the light source.

In a third aspect, a flow cytometer may have a light detection system comprising at least first and second light detectors and a dichroic mirror unit with a dichroic mirror disposed to receive light along the second optical path and to direct different portions of the received light from the dichroic mirror to each of the first and second light detectors. The dichroic mirror unit may include the dichroic mirror mounted on a rotatable mount that is rotatable to adjust angular positioning of the dichroic mirror.

A number feature refinements and additional features are applicable to any or all of a flow cytometer of any of the first, second and third aspects, or to other aspects of this disclosure. Such feature refinements and additional features may be used individually or in any combination and with any one or more aspects of this disclosure. As such, each of the following features may be, but are not required to be, used with any other feature or combination of features of the same or any other aspect or aspects of this disclosure.

A flow cytometer of any of the first, second or third aspect may include any feature or features of one or more other such aspect. For example, a flow cytometer of the first aspect may include as optical components of the flow cytometry optical system assembly a mirror unit according to the second aspect and/or a dichroic mirror unit and first and second detectors of the third aspect. As another example, a flow cytometer of the second aspect may include the dichroic mirror and first and second detectors of the third aspect.

When a flow cytometer includes a flow cytometer optical system assembly supported by a vibration isolation structure when the flow cytometer is in an operational configuration, a number of feature refinements and additional features may be applicable.

By vibration isolation, it is not meant that there is no transmittance of mechanical energy across the vibration isolation structure to a flow cytometry optical system assembly supported by the vibration isolation structure. The vibration isolation structure provides for reduced transmittance of mechanical energy at least at some frequencies.

A vibration isolation structure may be a passive vibration isolation design, and may include a vibration isolation material that supports the entire weight of the flow cytometry optical system assembly when the flow cytometer is in an operational configuration, and such vibration isolation material may be in compression between the platform and a rigid support structure that supports the vibration isolation material. A vibration isolation material may have compliancy that helps to reduce transmittance of vibrations across the vibration isolation structure, at least for vibrations with a significantly higher frequency than a natural frequency of the vibration isolation material. A vibration isolation material may have a Shore A durometer hardness in range having a lower limit of 10, 20, 30, 40 or 45 and an upper limit of 100, 90, 80, 70, 60 or 55. In some implementations the Shore A durometer hardness of vibration isolation material may be about 50. A vibration isolation material may be an elastomeric material. Such elastomeric material may be a rubber material, which may be a natural or synthetic rubber material. Vibration isolation material may be a polymer material, which may be a thermoplastic polymer composition or may be a thermoset polymer composition. Such a polymer material may include a neoprene, a ethylene propylene diene monomer rubber (EPDM rubber), a nitrile butadiene rubber (NBR), a silicone rubber, a polybutadiene, a polyisobutylene, a polyisoprene, a polymethyl methacrylate (PMMA), a polyurethane, a styrene-butadiene rubber (SBR) or a polyolefin (e.g., polyethylene). Such a polymer material may include one or more additives, for example fillers, plasticizers, stabilizers, etc. In some preferred implementations, vibration isolation material may comprise neoprene.

A vibration isolation structure on which a flow cytometry optical system assembly is supported may be disposed entirely within the enclosure of the flow cytometer. The vibration isolation structure may comprise a plurality of vibration isolation mounts on which the support platform of the assembly is mounted. The vibration isolation mounts may include a vibration isolation material, for example as summarized above, to provide compliancy to the vibration isolation mount. A vibration isolation mount may have a spring rate in compression of at least 5, at least 10, at least 20 or at least 30 N/mm. The spring rate in compression may be up to 200, up to 150, up to 100, up to 75, up to 50 or up to 40 N/mm. A vibration isolation mount may have a spring rate in shear of at least 1, at least 2, at least 3 or at least 4 N/mm. The spring rate in shear may be up to 50, up to 30, up to 20, up to 15, up to 10 or up to 6 N/mm. Such vibration isolation mounts may be supported by rigid support members, which may include a structure in which each vibration isolation mount corresponds with and is supported by a different such support member. Such support members may be disposed within the enclosure of the flow cytometer. The rigid support structure may include at least 2, at least 3 or more of the support members. The vibration isolation structure may include at least 2, at least 3 or more of the vibration isolation mounts. All or less than all of the rigid support members may be associated with a corresponding vibration isolation mount. The rigid support structure may be disposed entirely within the enclosure.

When the flow cytometer includes a vibration isolation structure, the flow cytometer may include a reconfigurable protection structure that may have one configuration when the flow cytometer is in an operational configuration and a different configuration when the flow cytometer is a shipping configuration with protection being afforded to the vibration isolation structure to reduce potential for damage to the vibration isolation structure during shipping and handling of the flow cytometer. The protection structure may provide at least protection to the vibration isolation structure from shear stress that may result from relative lateral movement between the support platform and the shear protection structure, and may be referred to herein as a "shear protection structure" even though the protection structure may also provide protection for other stress, such as tensile stresses to which the vibration isolation structure could be subjected in the event that the support platform and vibration isolation structure were subjected to forces that would pull them apart during shipping or handling. The shear protection structure may be movable between a first position in which the shear protection structure is positioned to provide protection to the vibration isolation structure from damage by shear stresses and a second position in which the shear protection structure is not positioned to provide protection to the vibration isolation structure from damage by shear stresses. When the flow cytometer is in the operational configuration the shear protection structure is in the second position, and when the flow cytometer is in the shipping configuration the shear protection structure is in the first position. The shear protection structure may be retainable in the first position to relieve the vibration isolation structure from supporting at least a portion of the weight of the flow cytometry optical system assembly that may be supported by the vibration isolation structure when the shear protection structure is in the second position. The shear protection structure may be such that when in the first position the shear protection structure may be attachable to the support platform to prevent lateral movement between the support platform and the vibration isolation structure. When the vibration isolation structure comprises a plurality of vibration isolation mounts supported by support members, the vibration isolation mounts may extend above the corresponding support member, and the shear protection structure may include a one or more protection members, with each protection member in the first position attachable to both the support member and the support platform to rigidly fix the support member to the support platform to prevent relative movement of the support platform and the support member. In the second position the protection member may be not attachable to the support platform and the support member to provide such rigid fixation. In some implementations, such a protection member may be in the form of a slidable member that is slidable relative to a support member between the first position and the second position. Such a slidable member may be in the form of a slidable sleeve that is slidable relative to a support member and in which a portion of the vibration isolation mount extending above the support member may be disposed when the shear slidable member is in the first position but not when the shear slidable member is in the second position. A flow cytometer may include at least 2, at least 3 or more of such slidable members with each said slidable member corresponding to a different support member and corresponding vibration isolation mount. In other implementations such a protection member may be not designed to be slidable relative to a support member. A protection member may be pivotable relative to a support member between the first and second positions, or may be completely removable from the vicinity of the support member when in the second position.

The vibration isolation structure that supports the flow cytometry optical system assembly when a flow cytometer is in an operational configuration provides vibration isolation to the support platform and components supported on the support platform relative to vibrations propagating through the enclosure and other components of the flow cytometer. Such a vibration isolation structure may be a first vibration isolation structure, and for additional vibration isolation protection the flow cytometer may include a second vibration isolation structure that supports the flow cytometer enclosure at least when the flow cytometer is in the operational configuration. Such a second vibration isolation structure may provide additional vibration isolation protection, for example by providing a vibration propagation barrier to the enclosure and contents within the enclosure, with the first vibration isolation structure providing a further vibration propagation barrier between the enclosure and the flow cytometry optical system assembly. The second vibration isolation structure may include a second vibration isolation material on which the entire weight of the enclosure and contents within the enclosure are supported. The second vibration isolation material may be the same as or different than the vibration isolation material of the first vibration isolation structure, and may for example be of any material and be of any hardness as described above for the first vibration isolation structure. The second vibration isolation structure will carry more weight than the first vibration isolation structure, and in some implementations, the second vibration isolation material of the second vibration isolation structure may have a hardness that is larger than the hardness of the vibration isolation material of the first vibration isolation structure, and which may be larger by an amount of at least 10, or at least 20 Shore A hardness durometer units. The second vibration isolation structure may be in the form of feet, or vibration isolation mounts that are designed to rest on a counter, table or other supporting work surface. Such second vibration isolation mounts, or feet, may have a spring rate in compression and/or in shear as described above for the vibration isolation mounts (first vibration isolation mounts) to support a flow cytometry optical system assembly within the enclosure, although such second vibration isolation mounts may often have higher spring rates in compression and in shear than the first vibration isolation mounts.

The support platform of a flow cytometry optical system assembly may be made of a much more hard and rigid material than a vibration isolation material of a vibration isolation structure on which the support platform may be supported. The support platform may be made of a hard plastic material, but in preferred implementations is made of a metallic material of construction. In some implementations, the support platform may be of a material of construction having a hardness of at least 10, at least 20, at least 40 or at least 50 on a Rockwell B hardness scale. One preferred material of construction for the support platform is aluminum, which may be in the form of a cast aluminum composition. Using aluminum provides significant strength to the support platform while keeping down weight that must be supported by a vibration isolation structure on which the support platform may be supported. The support platform may be a unitary structure disposed within the enclosure. The support platform may be formed of multiple connected pieces or may be formed of a single piece. The support platform may be in the form of a frame or other structure with openings through the structure, or may be a shelf-like structure without openings through the structure. The support platform may have geometric features for keying with corresponding components to be mounted on the support platform, for example recesses, protrusions or other surface features that may key with and help properly locate or orient components supported on the support platform. A support platform may have supported thereon components other than optical components, for example flow conduits, fluid flow sensors, wiring or other equipment.

When a flow cytometer includes a flow cytometry optical system assembly, the flow cytometry optical components supported by the support platform will typically include at least component units including a light source, a flow cell and at least one light detector. When reference is made herein to a component unit (such as for example a light source unit, mirror unit, flow cell unit or dichroic mirror unit), the unit may be made up of only the corresponding optical element (e.g., a light source, mirror, flow cell or dichroic mirror) or an assembly including the optical element with other elements, for example to support, retain, enclose or facilitate adjustment of the optical element (e.g., holders, frames, housings, mounts, connectors, adjustment screws or motors, etc.). Such flow cytometry components supported by the support platform may include a mirror unit including a mirror disposed along the first optical path between the light source and the flow cell, and the mirror may be adjustable within the mirror unit to adjust orientation of the mirror relative to the light source. For example, a flow cytometer according to the second aspect includes a mirror unit with an adjustable mirror. Flow cytometry optical components supported by the support platform may comprise a lens unit with a focusing lens disposed along the first optical path between the mirror and the flow cell to focus light from the light source toward the investigatory flow path. Flow cytometry optical components supported by the platform may include a dichroic mirror unit including a dichroic mirror disposed along the second optical path between the flow cell and the light detector. Such a dichroic mirror may be adjustable within the dichroic mirror unit to adjust orientation of the dichroic mirror relative to the light detector. The dichroic mirror may be a part of a light detection assembly including at least two light detectors, with a first light detector oriented to receive a first wavelength range of light passing through the dichroic mirror and a second light detector oriented to receive a second wavelength range of light reflected by the dichroic mirror. A first wavelength range corresponds with a first fluorescent emission wavelength of a first fluorescent stain indicative of the presence of a first biological material and the second wavelength range includes a second fluorescent emission from a second fluorescent stain indicative of the presence of a second biological material. For example, in applications involving detection of virus particles, one fluorescent stain may associate with protein and another fluorescent stain may associate with nucleic acid, and simultaneous detection of the two different fluorescent emission signatures may be indicative of the presence of in-tact virus particles in a sample fluid.

The flow cytometry optical components supported on a support platform of a flow cytometry optical system assembly may be supported in a manner such as to be retained in the flow cytometry optical system assembly with fixed relative positioning for flow cytometry operation, and the flow cytometry optical system assembly may be removable from the enclosure as a unit with the flow cytometry optical components retained in the fixed relative positioning as supported by the support platform. This provides for good stability of flow cytometer components over a prolonged period of use and facilities ease of manufacture and servicing the flow cytometry optical system assembly and components thereof.

In some preferred implementations, a flow cytometry optical system assembly includes a light source unit that does not permit adjustment of the orientation of light emitted from the light source along the first optical path. Rather, adjustability is provided with an adjustable mirror disposed on the first optical path. Likewise, in some preferred implementations, positioning of light detectors is not adjustable relative to the dichroic mirror. Adjustability may be provided by the adjustability of the dichroic mirror instead. The flow cell unit of a flow cytometry optical system assembly may include a flow cell that is mounted in the flow cell unit to provide for adjustability of the flow cell within the flow cell unit to adjust orientation of the flow cell relative to one or more optical components on the first optical path and one or more components on the second optical path. Optical components supported on a support platform may include a spatial filter (e.g., pinhole filter) disposed along the second optical path to spatially filter light prior to detection, such as to filter light between the investigatory flow path of the flow cell and a dichroic mirror.

When a flow cytometer includes a dichroic mirror mounted on a rotatable mount, the rotatable mount may be rotatable to adjust positioning of the dichroic mirror, for example to to alter an incident angle of light on the dichroic mirror received from the second optical path. The rotatable mount may be rotatable about an axis generally perpendicular to the direction of light travel. The rotatable mount may be rotatable to adjust angular positioning of the dichroic mirror relative to the second optical path and/or relative to the first and second light detectors. The dichroic mirror may be disposed within a housing with the rotatable mount engaged with and rotatable relative to a mount seat in the housing. First and second light detectors may be in optical communication with the dichroic mirror disposed within the housing, and may be connected with the housing, which connection may be through band-pass filter units disposed between the dichroic mirror and the light detectors. The dichroic mirror, as mounted on a rotatable mount, may be within a light-tight enclosure with respect to ambient light penetration into the housing. A flow cytometer enclosure may provide a level of light penetration from outside of to inside of the enclosure. The dichroic mirror unit disposed within such an enclosure provides additional protection to ambient light that might be present within the enclosure, either due to outside light penetrating into the enclosure or light generated by componentry within the enclosure. The housing will, however, be open to receive light along the first optical path from the investigatory flow cell and to direct light to light detectors. The dichroic mirror unit may include a locking mechanism to lock in place the rotatable mount to fix the angular positioning of the dichroic mirror relative to the first and second light detectors. Such a locking mechanism may be reconfigurable between a locked configuration in which the rotatable mount is locked in position to prevent rotation of the rotatable mount and an unlocked position in which the rotatable mount is rotatable to adjust the angular positioning of the dichroic mirror. The locking mechanism may include one or more set screws that is each movable between an advanced position in the locked configuration to contact the rotatable mount and a retracted position in the unlocked configuration to not contact the rotatable mount.

Other aspects of this disclosure are directed to various methods involving a flow cytometer, such as a flow cytometer of any of the aspects summarized above.

In a fourth aspect, a method for preparing a flow cytometer for performing a flow cytometry investigation may include adjusting one or more adjustable optical components. When the flow cytometer includes a dichroic mirror unit with a dichroic mirror mounted on a rotatable mount, the method may include performing a flow cytometry investigation in the flow cytometer on a standard fluid with the rotatable mount rotated to a plurality of different positions corresponding with a plurality of different angular positionings of the dichroic mirror, after which a locking mechanism on the dichroic mirror unit may be locked to lock in place the rotatable mount to fix the angular positioning of the dichroic mirror relative to the light detectors. The different angular positioning may be relative to the second optical path and/or relative to the first and second light detectors. When the flow cytometer includes a mirror unit including an adjustable mirror disposed along the first optical path between the light source and the flow cell, the method may include adjusting the mirror to adjust orientation of the mirror relative to the light source. Adjusting the mirror may include performing flow cytometry investigation in the flow cytometer on a standard fluid with the mirror set at different orientations and then setting the mirror at an orientation based on an analysis of performance at the different orientations.

In a fifth aspect, a method for manipulating a flow cytometer to accommodate shipping or storage of the flow cytometer may include retaining a shear protection structure in a first position, when the flow cytometer includes a flow cytometry optical system assembly supported on a vibration isolation structure and a shear protection structure that is movable between a first position to protect the vibration isolation structure from damage by shear stresses when the flow cytometer is in a shipping configuration and a second position in which the shear protection structure does not provide protection to the vibration isolation structure from damage by shear stresses when the flow cytometer is in an operation configuration. In some variations, the method may include shipping the flow cytometer while the shear protection structure is retained in the first position. The method may include, after such shipping, releasing the shear protection structure from being retained in the first position and moving the shear protection structure to the second position. With the shear protection structure moved to the second position, the method may include performing a test flow cytometry investigation on a standard fluid to verify adequate performance of the flow cytometer and/or to assist in adjustment of one or more optical elements.

In a sixth aspect, a method for preparing a flow cytometer for performing a flow cytometer investigation may include releasing such a shear protection structure from being retained in the first position and moving the shear protection structure to the second position. This method may be performed even in the absence of shipping, for example after handling or after prolonged storage during which a vibration isolations structure is protected by the shear protection structure.

These and other aspects of the disclosure, and various feature refinements and additional features applicable thereto are provided in the drawings and in the further description provided below.

DETAILED DESCRIPTION

Figure 1:
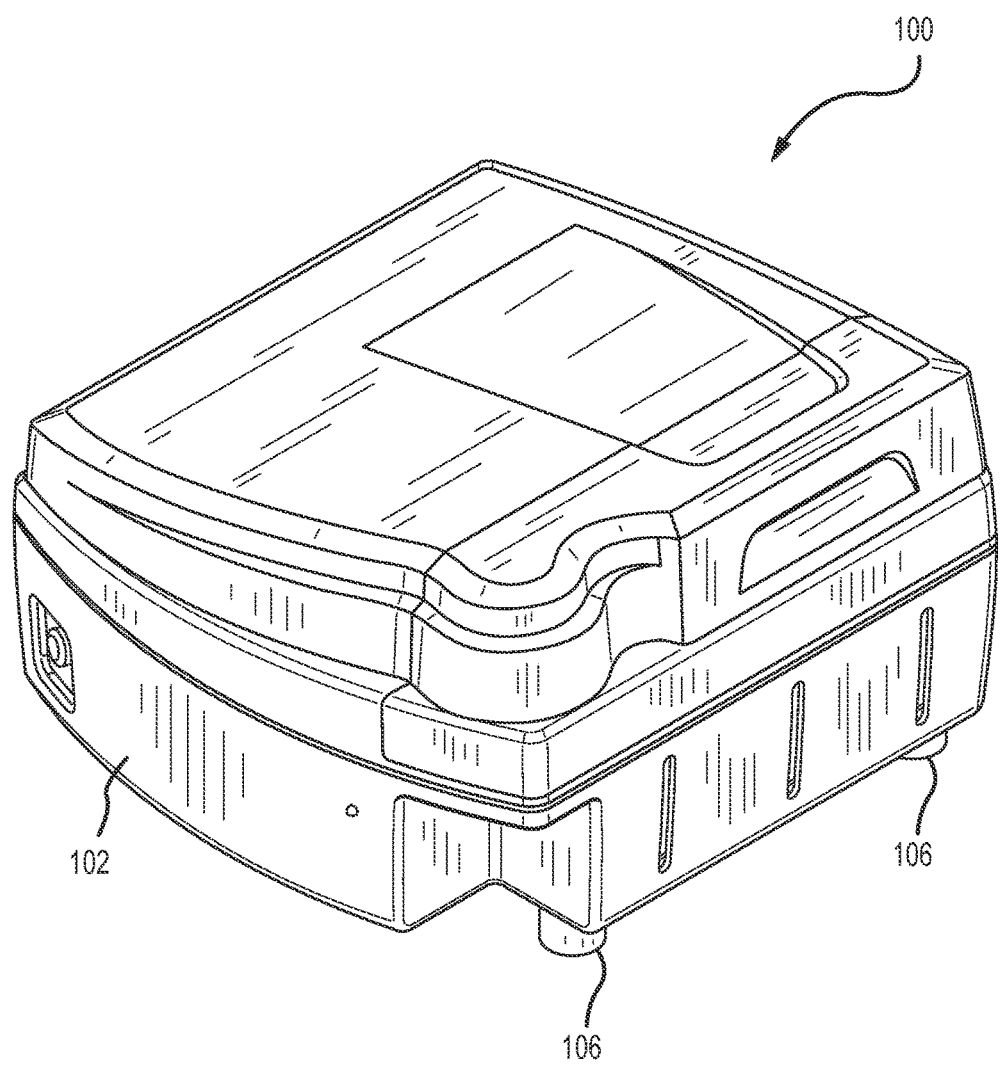
FIG. 1 shows a perspective view of a flow cytometer.
Figure 2:
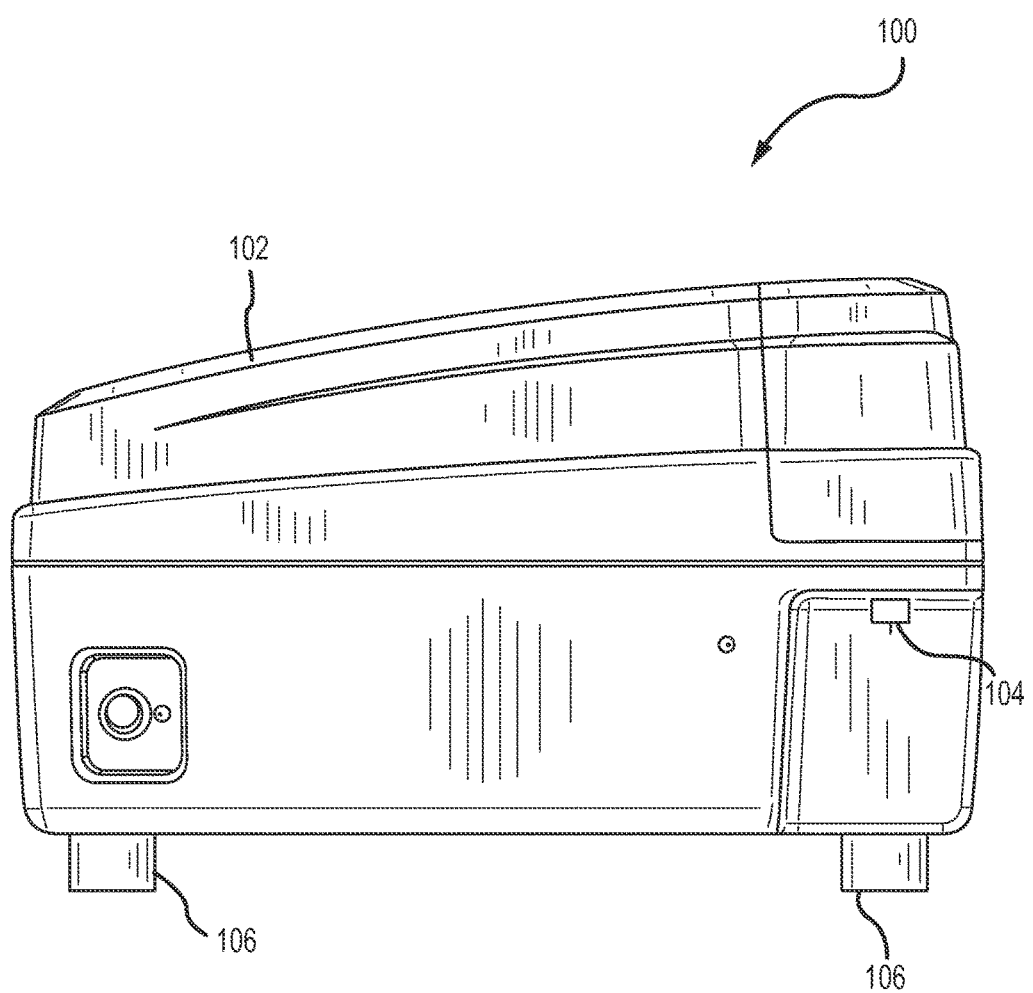
FIG. 2 shows an end view of the same flow cytometer as shown in FIG. 1.
Figure 3:
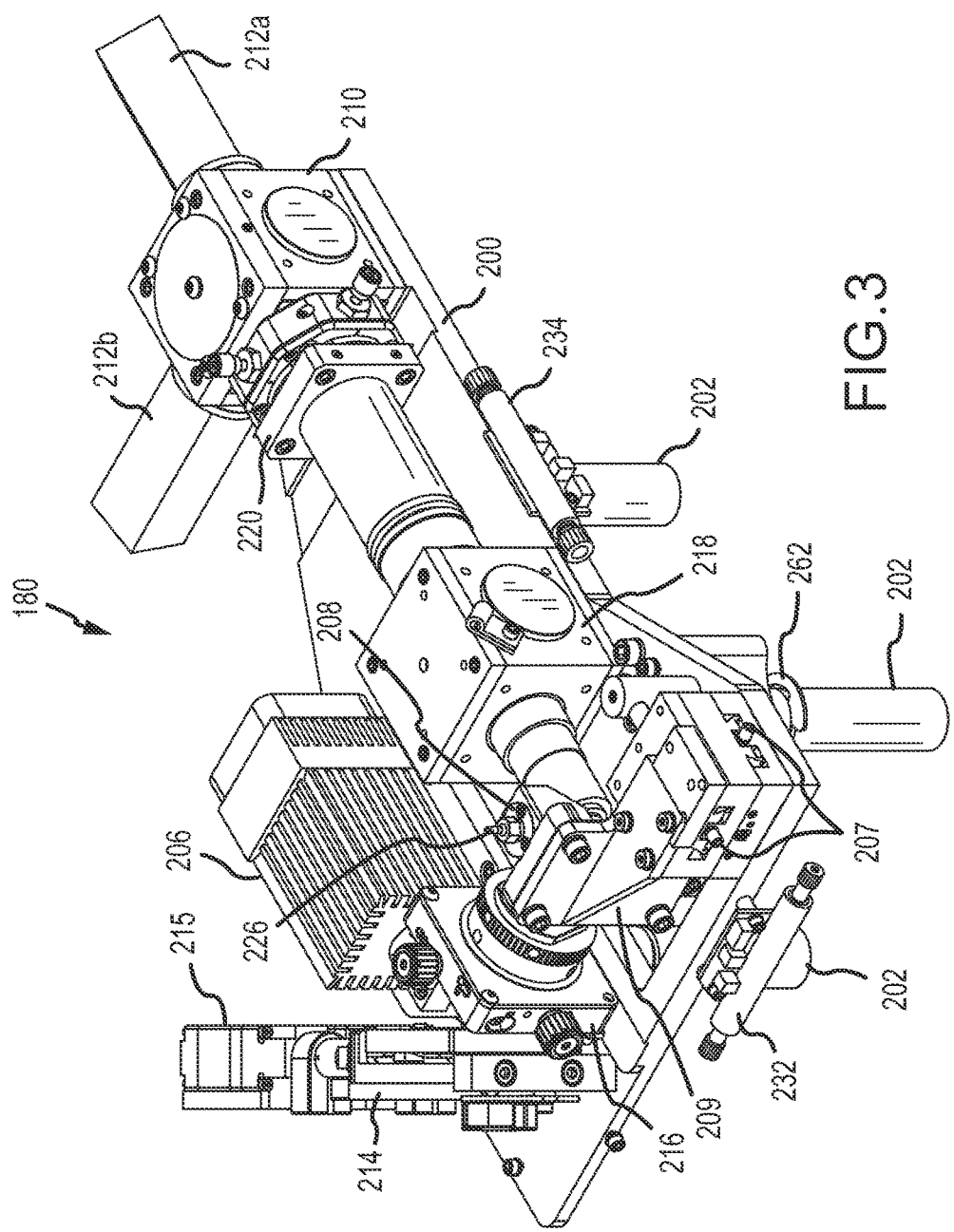
FIG. 3 is a perspective view of an example flow cytometer internal assembly that includes an example flow cytometry optical system assembly supported on an example vibration isolation structure.

Reference is made to FIGS. 1-10. FIGS. 1 and 2 show a flow cytometer 100 that includes flow cytometry componentry contained within a protective enclosure 102. Sample fluids to be tested may be introduced into the flow cytometer 100 for flow cytometry investigation through a sample inlet 104. The flow cytometer 100 includes resilient support pads 106, or feet, on which the weight of the enclosure 102 and contents within the enclosure 102 are supported, such as when the flow cytometer is situated on a shelf, counter, table or other surface for use. Advantageously, the support pads 106 may be of a material that provides significant vibration isolation to the enclosure 102, and to contents within the enclosure 102, from ambient environment vibrations that may be transmitted through such a surface on which the flow cytometer 100 is situated. The support pads 106 may, therefore, provide a vibration isolation structure that provides a vibration propagation barrier to the enclosure and contents within the enclosure.

FIGS. 3-10 show an example flow cytometer internal assembly 180, also referred to as a flow cytometry bench assembly, that may be disposed within the enclosure 102 of the flow cytometer 100. The flow cytometer 100 may also include other equipment or components disposed within the enclosure (e.g., sample fluid container, sheath fluid container, reagent containers, tubing, etc.). The internal assembly 180 includes a flow cytometry optical system assembly including a support platform 200 and a number of flow cytometry optical components supported by the support platform 200, with the optical components retained on the platform with fixed positioning to facilitate performance of flow cytometry investigations of sample fluids using the optical components. The flow cytometry optical system assembly is supported by a support structure including three rigid support members 202 and corresponding vibration isolation mounts 204 that are supported by the support members 202 and on which the entire weight of the support platform 200 and components supported by the support platform 200 are supported during performance of flow cytometry investigations.

The flow cytometry optical components supported by the support platform 200 include a light source unit in the form of a laser unit 206 including a laser light source, a flow cell unit 208 and a light detection system including a dichroic mirror unit 210 and two light detectors 212, for example photomultiplier tubes. During operation of a flow cytometry investigation of sample fluid flowing through an investigatory flow path of a flow cell of the flow cell unit 208, light from the laser unit 206 travels along a first optical path to the flow cell to illuminate at least a portion of the investigatory flow path in the flow cell. The first optical path includes a mirror unit 214 that includes a mirror that reflects light from the laser unit 206 to direct that reflected light through a focusing lens 216 to focus light in the vicinity of the investigatory flow path within the flow cell of the flow cell unit 208. Light from the investigatory flow path of the flow cell is directed along a second optical path from the flow cell to the dichroic mirror unit 210 for detection by the light detectors 212. The second optical path includes a focusing lens unit 218 and a spatial lens unit 220 between the flow cell unit 208 and the dichroic mirror unit 210. A dichroic mirror within the dichroic mirror unit 210 splits the light between some light wavelengths that pass through the dichroic mirror and are directed toward light detector 212a and other light wavelengths that are reflected by the dichroic mirror and are directed toward light detector 212b. Band-pass filter units 222 may be disposed in the optical paths to the light detectors 212 to pass a narrow wavelength range of light including a wavelength or band of wavelengths targeted for detection by the respective light detectors 212. This disclosure is presented with primary reference to use of preferred light sources including a laser to provide light, but the aspects disclosed are not limited to use of a laser as a light source. For example, an alternative light source could include one or more LED lights.

Figure 11:
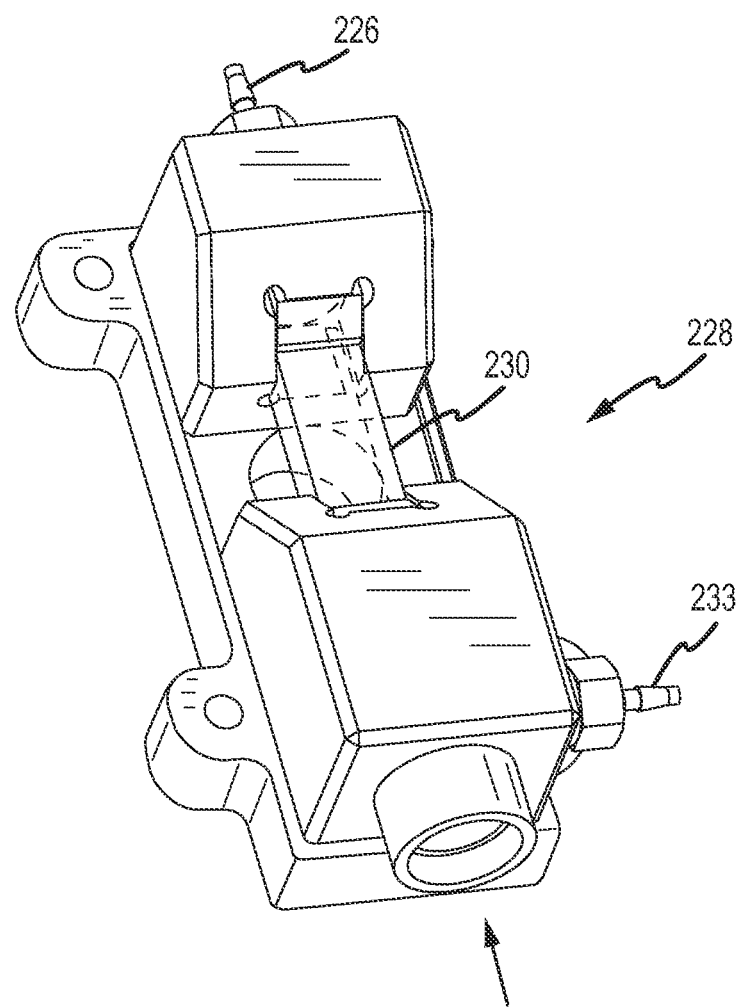
FIG. 11 is a perspective view of an example flow cell.

During operation of the flow cytometer 100 to perform a flow cytometry investigation of a sample fluid, the sample fluid to be investigated may be introduced into the flow cytometer through the sample inlet 104. The sample fluid is conducted, for example through tubing or other conduits, to an inlet 224 to the flow cell unit 208. The sample fluid flows through the investigatory flow path in the flow cell and exits the flow cell unit 208 through a sample exit 226. An example of a flow cell 228 of the flow cell unit 208 is shown in FIG. 11. As shown in FIG. 11, sample fluid is introduced into one and of the flow cell 228 as shown by the arrow and flows through a transparent section 230 where it is subjected to light from the laser unit 206. The investigatory flow path passes through the transparent section 230. The transparent section 230 may, for example, be made of a quartz crystal material.

Referring to FIGS. 1-11, between the sample inlet 104 of the flow cytometer 100 and the inlet 224 to the flow cell unit 208, the sample fluid passes through a fluid path that includes a flow meter 232 where the flow rate of the sample fluid flow to the flow cell 228 may be measured for data collection purposes and/or for use in feedback control to control the fluid sample flow rate to the flow cell unit 208. In the flow cell 228, a sheath fluid is introduced around the sample fluid flow before the sample fluid flows through the transparent section 230 for investigation. The sheath fluid is introduced into the flow cell 228 through a sheath fluid inlet 233, shown in FIG. 11. Prior to introduction of the sheath fluid into the flow cell 228, the sheath fluid passes through a fluid path that includes a flow sensor 234, where the flow rate of the sheath fluid flow to the flow cell 228 may be measured for data collection and/or for use in feedback control to control the flow rate of the sheath fluid to the flow cell 228. The flow sensors 232 and 234 are conveniently supported on the support platform 200. The sample fluid and sheath fluid combination flow through the transparent section 230 where the sample fluid is investigated by light from the laser unit 206, and then the sample fluid and sheath fluid exit the flow cell 228 through the sample exit 226. Flow cytometers are described herein with primary reference to preferred flow cytometer designs that include a sheath fluid (e.g., clean aqueous liquid) to help hydrodynamically focus a sample fluid through a flow cell. However, the aspects disclosed herein apply also to flow cytometers with designs that do not operate using a sheath fluid.

The laser unit 206, mirror unit 214, flow cell unit 208, dichroic mirror unit 210 and light detectors 212 may all be retained on the support platform 200 with fixed positioning. However positioning of the mirror in the mirror unit 214, flow cell in the flow cell unit 208 and dichroic mirror in the dichroic mirror unit 210 are all adjustable within the respective units as supported by the support platform 200. The mirror of the mirror unit 214 is adjustable in two axes (e.g., tip and tilt) by operation of two linear step motors 215 that are actuatable to reorient the mirror through tip and tilt adjustments, respectively. The positioning of the flow cell in the flow cell unit 208 is adjustable relative to the first and second optical paths through manipulation of two adjustment screws 207 to change the vertical and horizontal positioning of the flow cell 228 through movement of a flow cell mounting bracket 209 on which the flow cell 228 is mounted in the flow cell unit 208. Adjustability of the positioning of the dichroic mirror in the dichroic mirror unit 210 is discussed further below. Positioning of the flow cell 228 in the flow cell unit 208 and of the dichroic mirror in the dichroic mirror unit 210 may be set and locked in place at the factory or by a service representative with initial set-up at a customer site and may then be adjusted later if needed as part of servicing the flow cytometer. The positioning of the mirror in the mirror unit 214 may also be set in the factory or at the time of initial set-up at a customer site, but advantageously, the user of the flow cytometer 100 may reset positioning of the mirror occasionally to maintain a proper alignment with the laser unit 206. Repositioning of the mirror unit 214 may follow performance of user-initiated diagnostics to assess performance of the flow cytometer operating to analyze a standard fluid. The diagnostics may be user-initiated using a user interface, and after being initiated the diagnostics may be directed and evaluated by a computer controller, for example when the results of the diagnostics indicate that performance of the flow cytometer in analyzing the standard fluid is deficient. Adjustment of the positioning of the mirror in the mirror unit 214 may be user-initiated based on results of the diagnostics. Adjustment of the positioning of the mirror may be directed by a computer controller that evaluates performance of the flow cytometer on the standard fluid with the mirror set at different positions through actuation of the step motors 215. Based on monitored performance at different mirror positions, the mirror may be reset at a new position at which the flow cytometry performance is determined to be superior. Interposing the mirror unit 214 in the first optical path between the laser unit 206 and the flow cell unit 208 and providing a user-initiated ability to adjust positioning of the mirror in the mirror unit 214 for alignment with the laser unit 206 significantly enhances robustness of the flow cytometer 100 over extended periods of use and is significantly less complex and easier to control than attempting to adjust positioning of the laser of a laser light source, and may significantly reduce the need for service of the flow cytometer.

Reference to a standard fluid herein, is to a fluid of known composition, including particles of known size and composition in a known carrier liquid. Flow cytometer performance may be tested and potential problems may be diagnosed by performing a test flow cytometry investigation using the flow cytometer on the standard fluid. Flow cytometer results of a test run using a standard fluid may be compared to expected results indicative of proper performance of the flow cytometer. Flow cytometer testing using a standard fluid may be used to compare performance at different equipment settings to help set equipment parameters for more optimal flow cytometer performance. For example, a standard fluid may include synthetic particles of known size and composition (e.g., plastic spheres of known diameter) and at a known concentration in an aqueous carrier liquid.

Figures 12, 13:
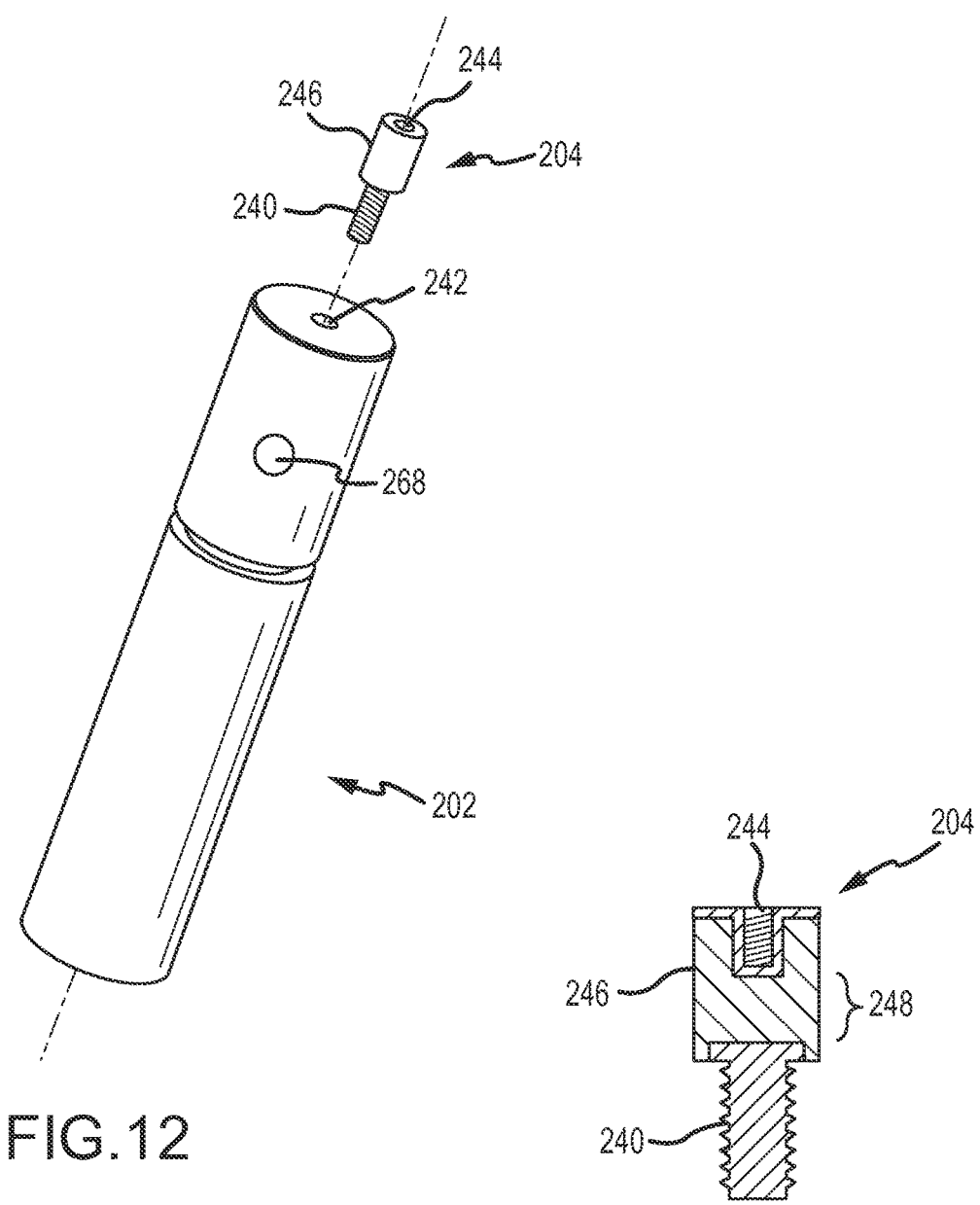
FIG. 12 is an expanded perspective view of an example support member and corresponding vibration isolation member.
FIG. 13 is a sectional view of the example vibration isolation member shown in FIG. 12.

With reference to FIGS. 1-10, 12 and 13, vibration isolation of the flow cytometry optical system assembly of the flow cytometer 100 will be further described. The vibration isolation mounts 204 provide a barrier to propagation of vibrations through the enclosure 102 and through other components within the enclosure 102 to the support platform 200 and to the optical components and other equipment supported by the support platform 200. There is a separate vibration isolation mount 204 associated with each of the support members 202, although only one of the isolation support mounts 204 is shown in FIGS. 1-10. FIG. 12 shows more particularly a combination of an example support member 202 and corresponding example vibration isolation mount 204. The vibration isolation mount 204 has an externally threaded extension member 240 that threads into a corresponding internally threaded recess 242 in the support member 202, to engage and connect the vibration isolation mount 204 with the support member 202 for stable support of the vibration isolation mount 204 by the support member 202. The vibration isolation mount 204 includes an internally threaded recess 244 opening at the top of the vibration isolation mount 204 to accept a corresponding externally threaded member (e.g., screw or bolt) to connect the vibration isolation mount 204 with the support platform 200, to stably and securely support the support platform 200 on the vibration isolation mount 204. The vibration isolation mount 204 includes a body portion 246 made of resilient vibration isolation material that provides primary vibration isolation protection to the support platform 200 and equipment supported by the support platform 200. FIG. 13 shows a sectional view through the example vibration isolation mount 204 of FIG. 12. The threaded extension member 240 and the threaded recess 244 may be made of a strong, rigid material such as a metallic composition, for example a steel composition, to make a strong and secure connection with the support member 202 and the support platform 200, respectively. However, as seen in FIG. 13, the vibration isolation mount includes a vibration isolation section 248 of vibration isolation material that separates and provides vibration isolation protection between the threaded extension member 240 and the threaded recess 244, thereby providing vibration isolation protection between the support member 202 and the support platform 200. When the flow cytometer 100 is in an operational configuration for performing a flow cytometry investigation on a sample fluid, the entire weight of the support platform and all equipment supported by the support platform 200 may be supported by the vibration isolation material of the vibration isolation mounts 204 through such vibration isolation sections 248.

With primary reference again to FIGS. 1-10 and 14, different configurational features of a shipping configuration and an operational configuration of the flow cytometer 100 will be further described. The internal assembly 180 shown in FIGS. 3-10 includes two slidable members in the form of sleeve members 260, each of which corresponds with and is slidable relative to a corresponding support member 202. A ring clip 262 is disposed in a corresponding recess area of the support member 202 to act as a stop to restrict the portion of the longitudinal length of the support member 202 over which the corresponding sleeve 260 member is slidable, so that each sleeve member 260 is movable between at least two positions. In a first position, the top of the sleeve member 260 is in contact with the support platform 200 and the bottom of the sleeve member 260 is elevated above the ring clip 262. In a second position, the bottom of the sleeve member 260 is in contact with the ring clip 262 and the top of the sleeve member 260 is spaced below and does not contact the support platform 200.

Figure 4:
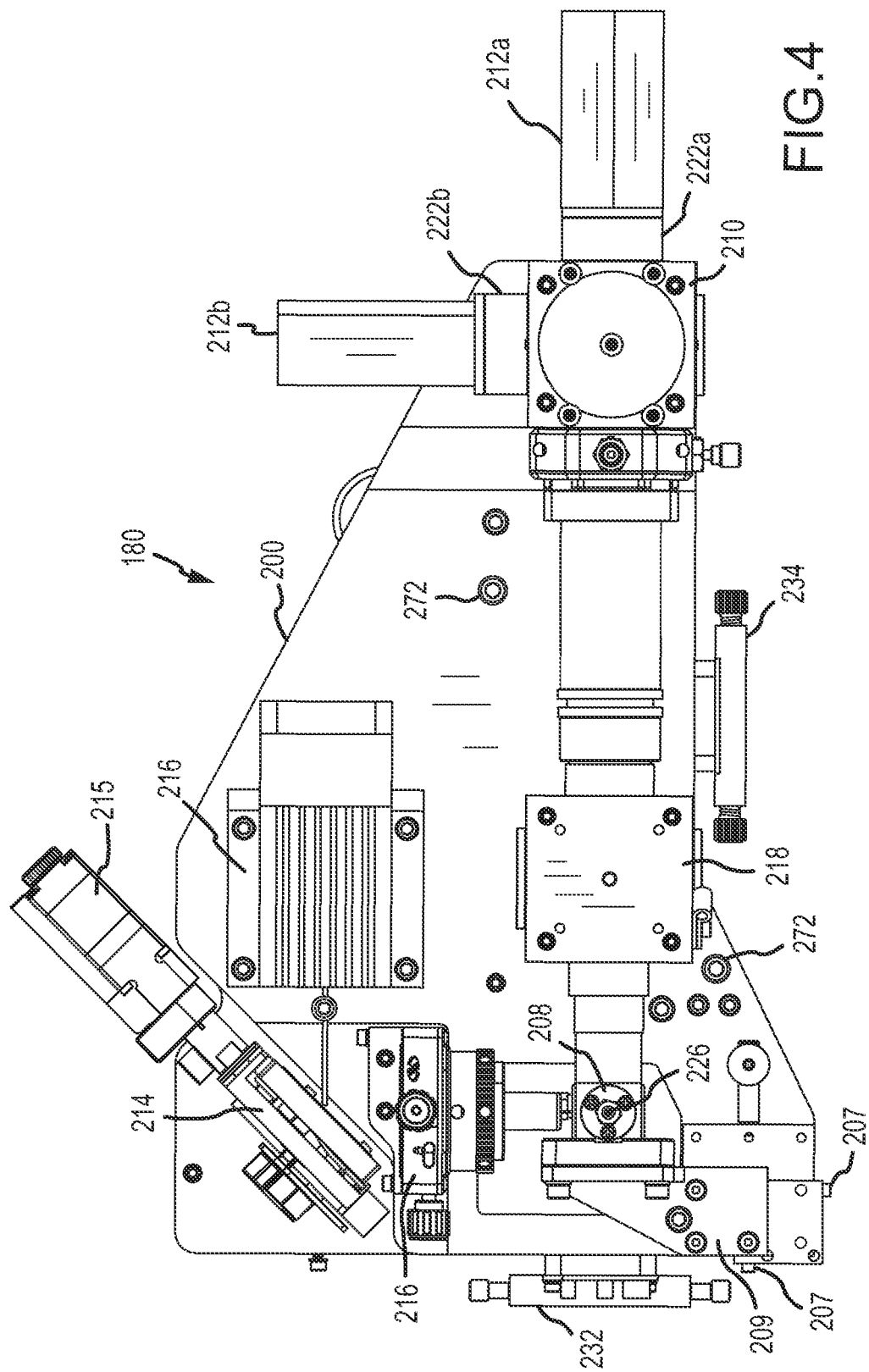
FIG. 4 is a top view of the example internal assembly of FIG. 3.
Figure 5:
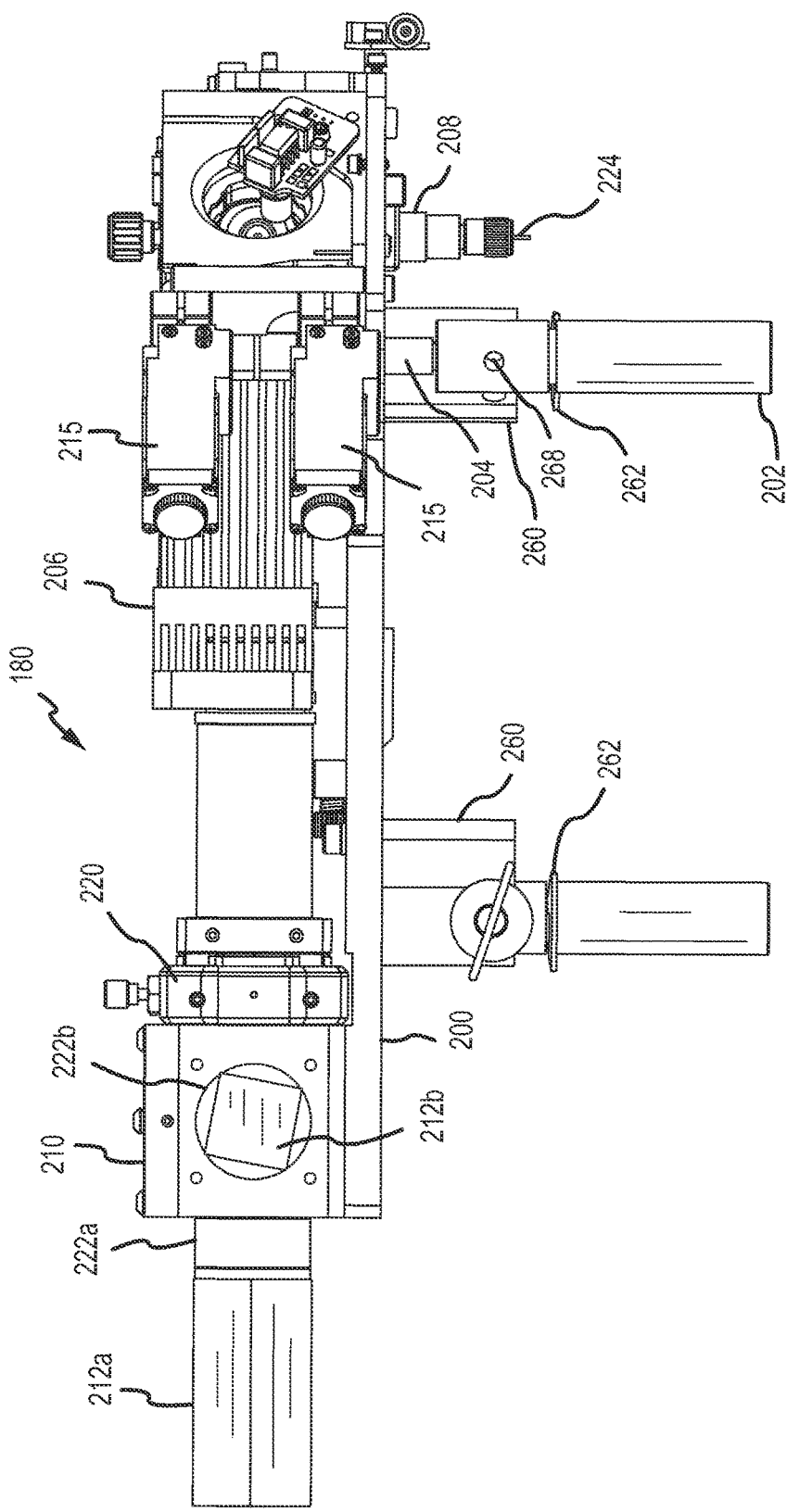
FIG. 5 is a side view of the example internal assembly of FIG. 3.
Figure 6:
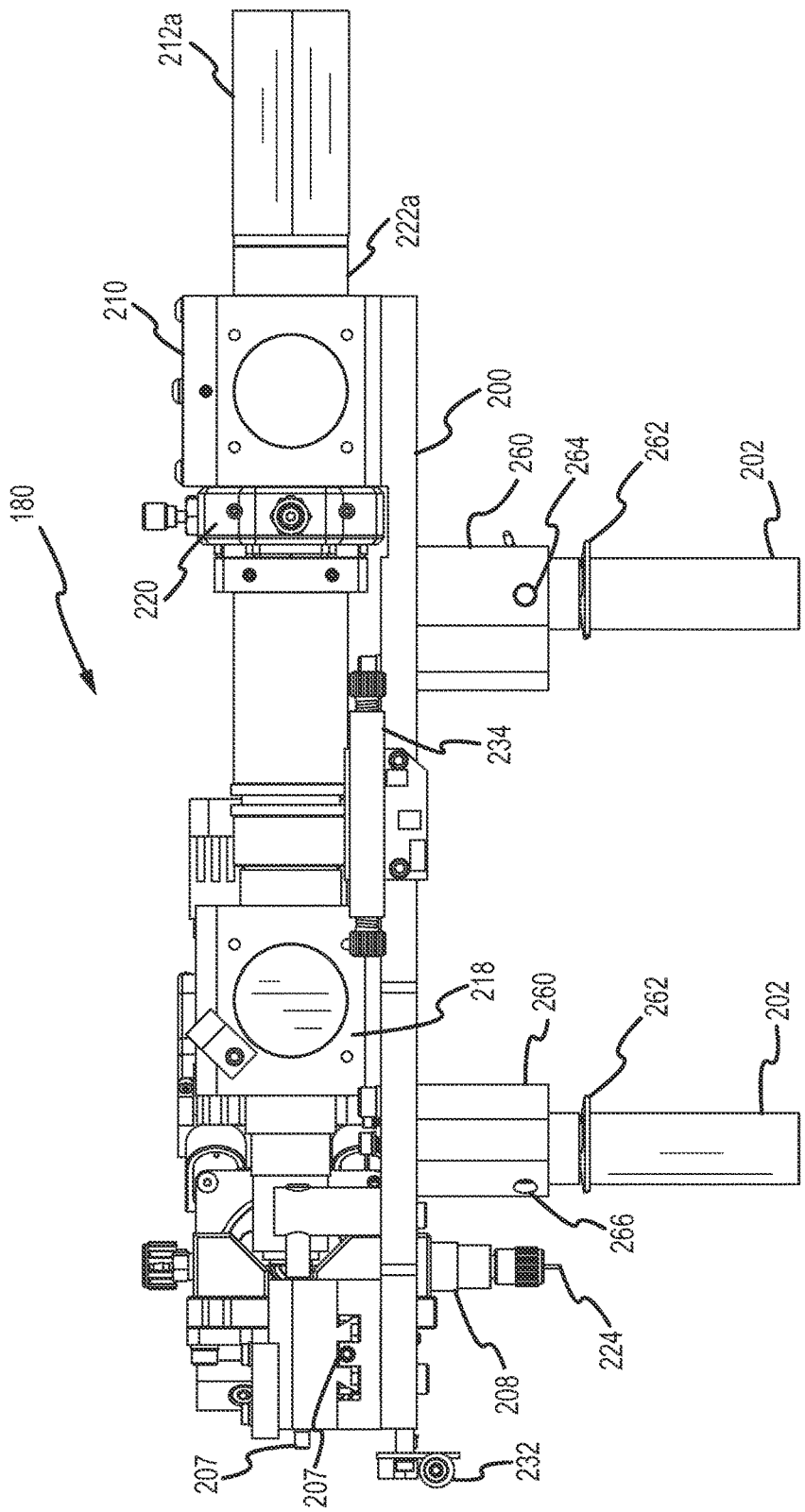
FIG. 6 is a side view of the example internal assembly of FIG. 3 viewed from an opposite side to that of FIG. 5.
Figure 7:
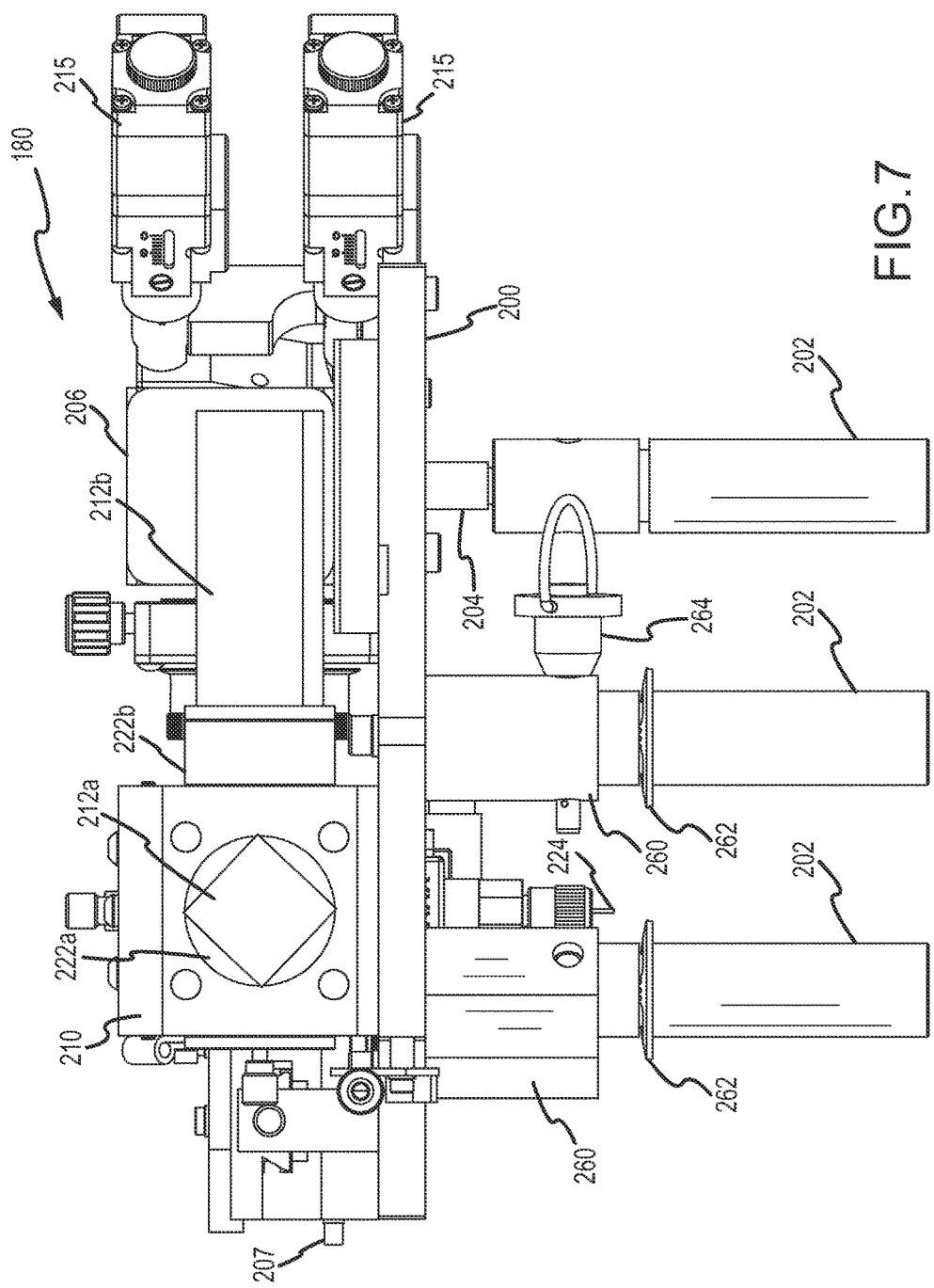
FIG. 7 is an end view of the example internal assembly of FIG. 3.
Figure 8:
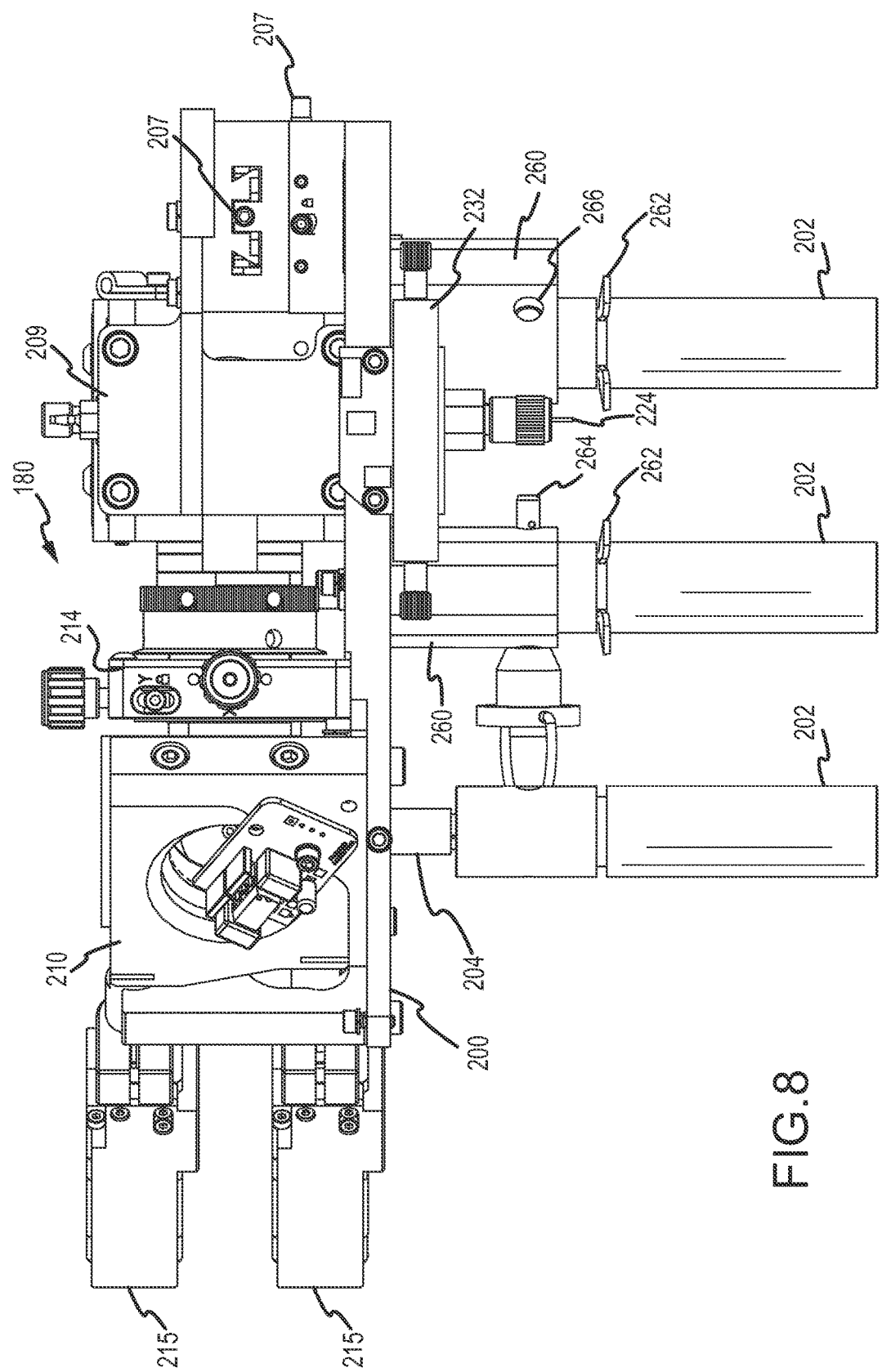
FIG. 8 is an end view of the example internal assembly of FIG. 3 viewed from an opposite end to that of FIG. 7.
Figure 9:
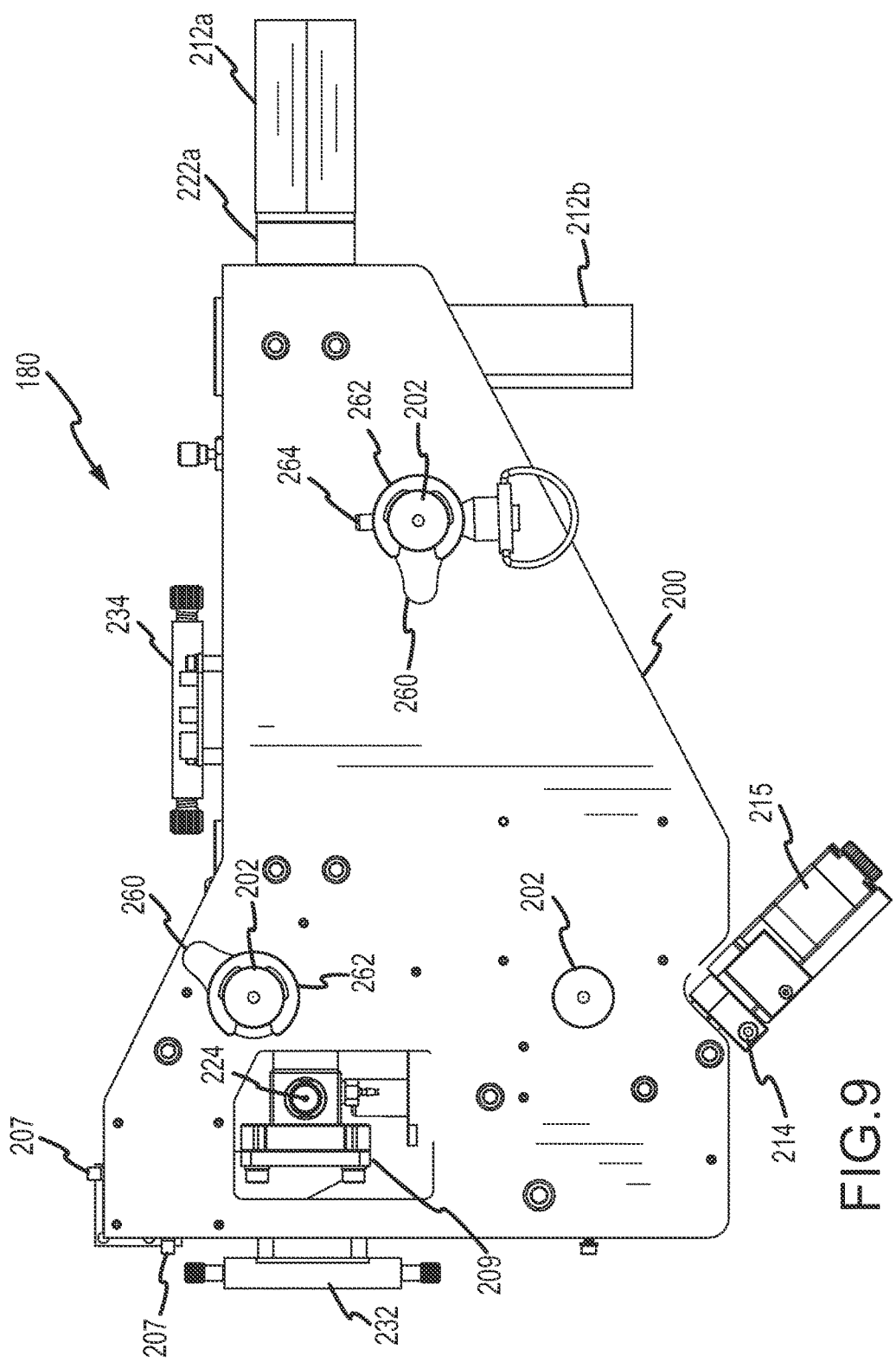
FIG. 9 is a bottom view of the example internal assembly of FIG. 3.
Figure 10:
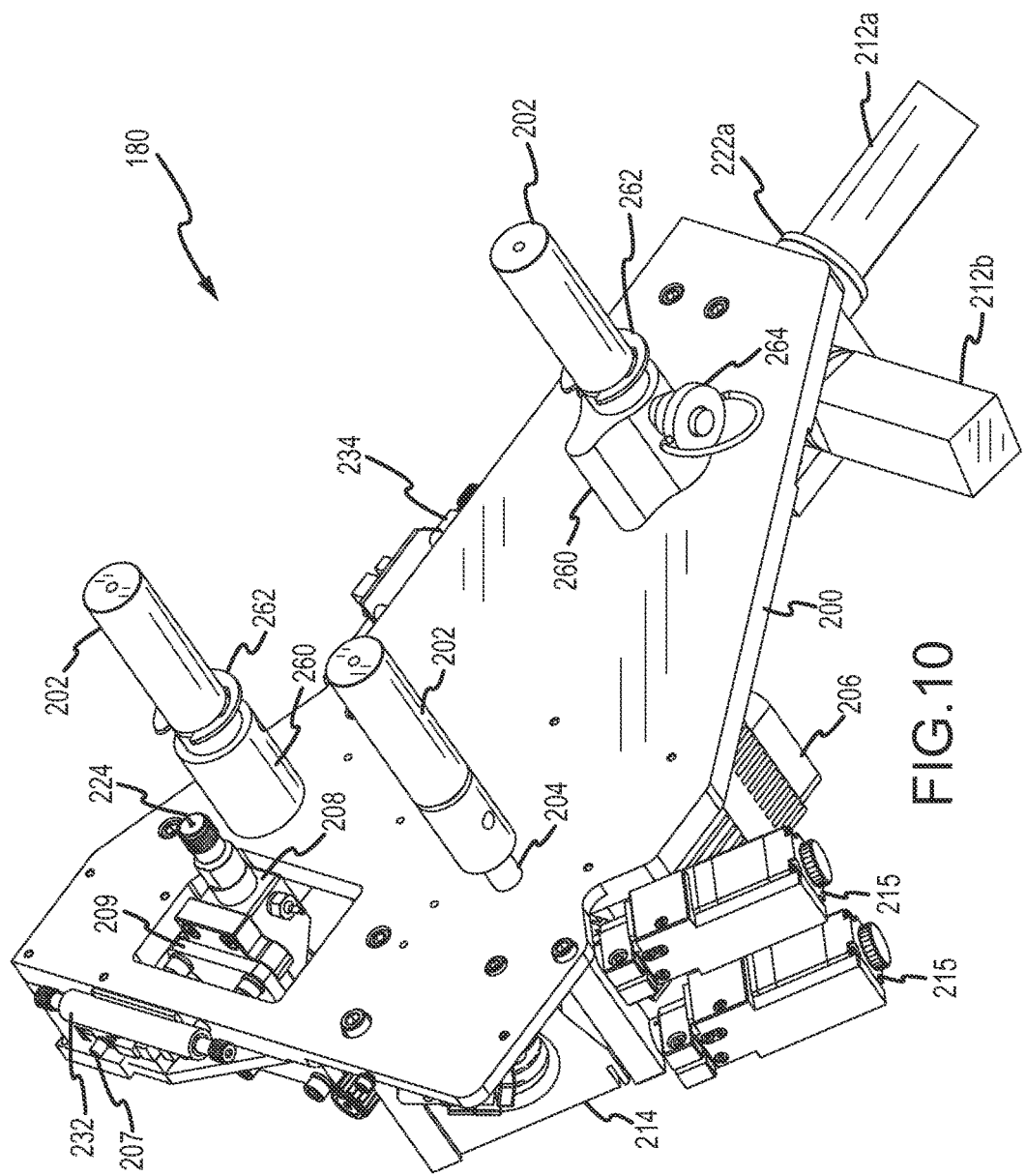
FIG. 10 is another perspective view of the example internal assembly of FIG. 3.
Figure 14:
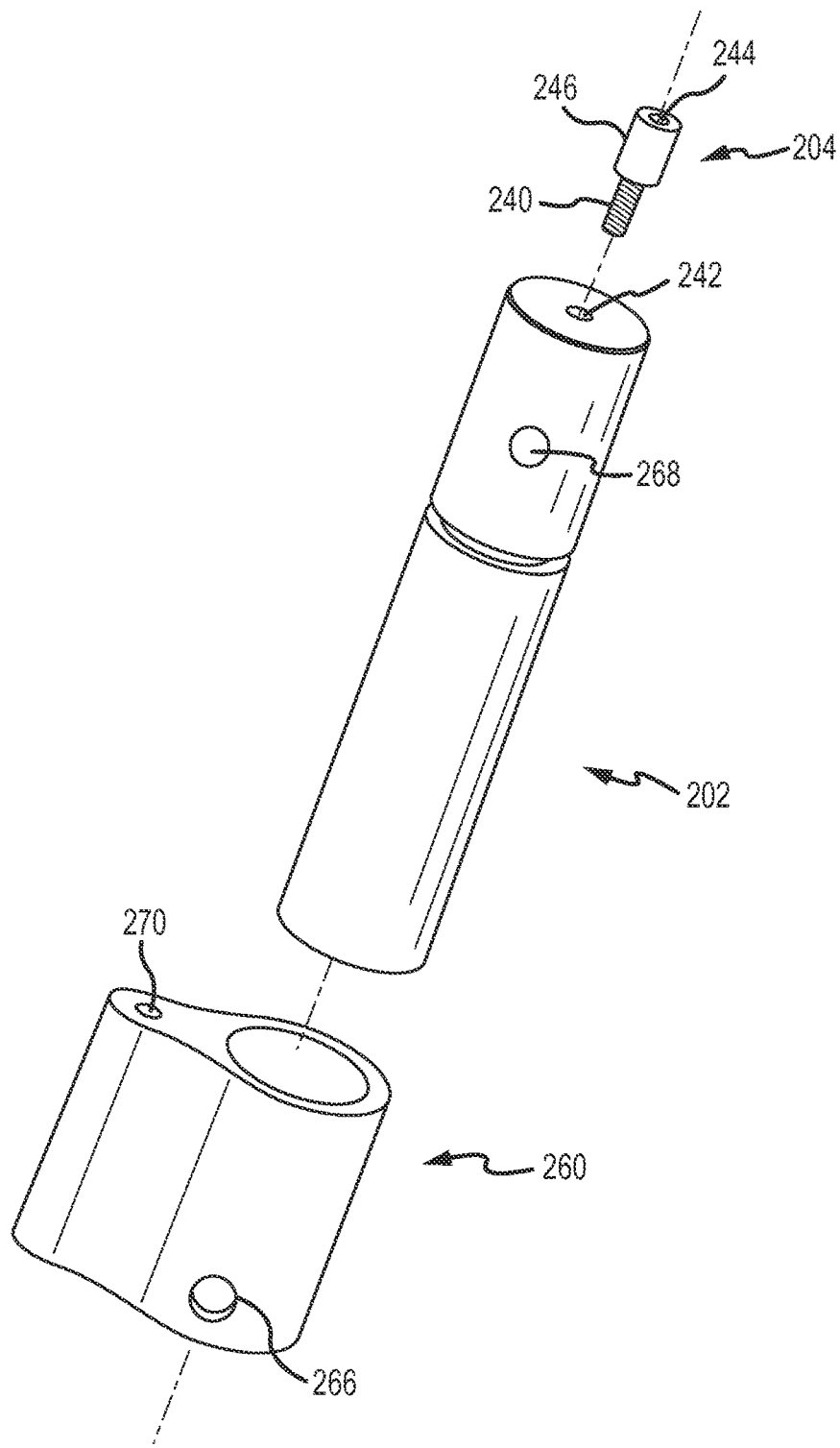
FIG. 14 is an expanded perspective view of an example of a combination of a support member with a corresponding vibration isolation member and slidable sleeve.

When the sleeve members 260 are in the first, raised position, the sleeve members 260 may provide protection to the vibration isolation mounts 204, for example during storage, shipping or handling. When the sleeves are in the second, lowered position, the internal assembly 180 may be in an operational configuration for performing flow cytometry investigations, with the vibration isolation mounts 204 supporting the weight of the support platform 200 and equipment supported on the support platform 200. In a shipping configuration, the sleeve members 260 are in the first, raised position, and each sleeve member 260 is retained in the first position by a pin 264 inserted through corresponding holes 266 and 268 through the sleeve member 260 and the corresponding support member 202, respectively. FIG. 14 shows a combination of a support member 202, isolation mount 204 and sleeve member 260. As shown in FIG. 14, the sleeve member 260 has an internally threaded receptacle 270 that corresponds with a corresponding hole through the support platform 200 to permit the sleeve member 260 to be connected with the support platform 200 by a threaded bolt or screw extending through the hole in the support platform 200 and threaded into the threaded receptacle 270. The sleeve members 260 are shown in FIGS. 3-10 retained in the first position by threaded bolts 272, the heads of which are shown in FIG. 4.

When the flow cytometer 100 is in a shipping configuration with the sleeve members 260 fixed in the first position by pins 264 and bolts 272, significant protection is provided to the vibration isolation mounts 204 to help prevent damage to the vibration isolation mounts 204 during shipping and/or other handling of the flow cytometer 100. The bolts 272 rigidly fix the corresponding support members 202 to the support platform 200 to limit lateral movement between the support members 202 and the support platform 200, and thereby provide protection to the vibration isolation mounts 204 from damage due to shear stresses across the vibration isolation mounts 204 that could otherwise result from relative lateral movement between the support platform 200 and the support members 202. The vibration isolation sections 248 (shown in FIG. 13) of the vibration isolation mounts 204 are particularly vulnerable to such shear damage due to sharp jolts or bumps that could occur for example during shipping or handling. Retaining the sleeve members 260 relative to the corresponding support members 202 further enhances the protection provided to the vibration isolation members 204. A sleeve member 260 fixed in the first position and connected to the support member 202 by the bolt 272 and connected to the support member 202 by the pin 264 prevents separation of the support platform 202 from the vibration isolation mount 204, which could result in subjecting the vibration isolation material of the vibration isolation mount 204 to excessive tensile stress that could damage or cause failure of the vibration isolation material, for example if the flow cytometer were to be turned upside-down during shipping or handling. Also, the holes 266 and 268 (shown in FIG. 14) on the sleeve member 260 and support member 202, respectively, may have relative positioning so that when fixed in position with the pin 264, the top of the sleeve member 260 may bear upward on the bottom of the support platform 200 to relieve the vibration isolation mounts 204 of at least some of the weight of the support platform 200 and equipment supported by the support platform 200. After shipping or handling, or after prolonged storage, the flow cytometer may be prepared for use to perform flow cytometry investigations on sample fluids. After being situated in the desired position for use, the pins 264 and the bolts 272 are removed and the sleeve members 260 are permitted to slide down the corresponding support members 202 to rest on the corresponding ring clips 262, in the second position. As seen in FIGS. 3-10, even though there are three support members 202 in the example internal assembly 180, only two of the support members 202 are fitted with sleeve members 260, which may be adequate to rigidly fix the positioning of the support platform 200 relative to all support members 202 and vibration isolation mounts 204. However, an additional sleeve member 260 could be fitted over the third support member 202 for added security.

Figure 15:
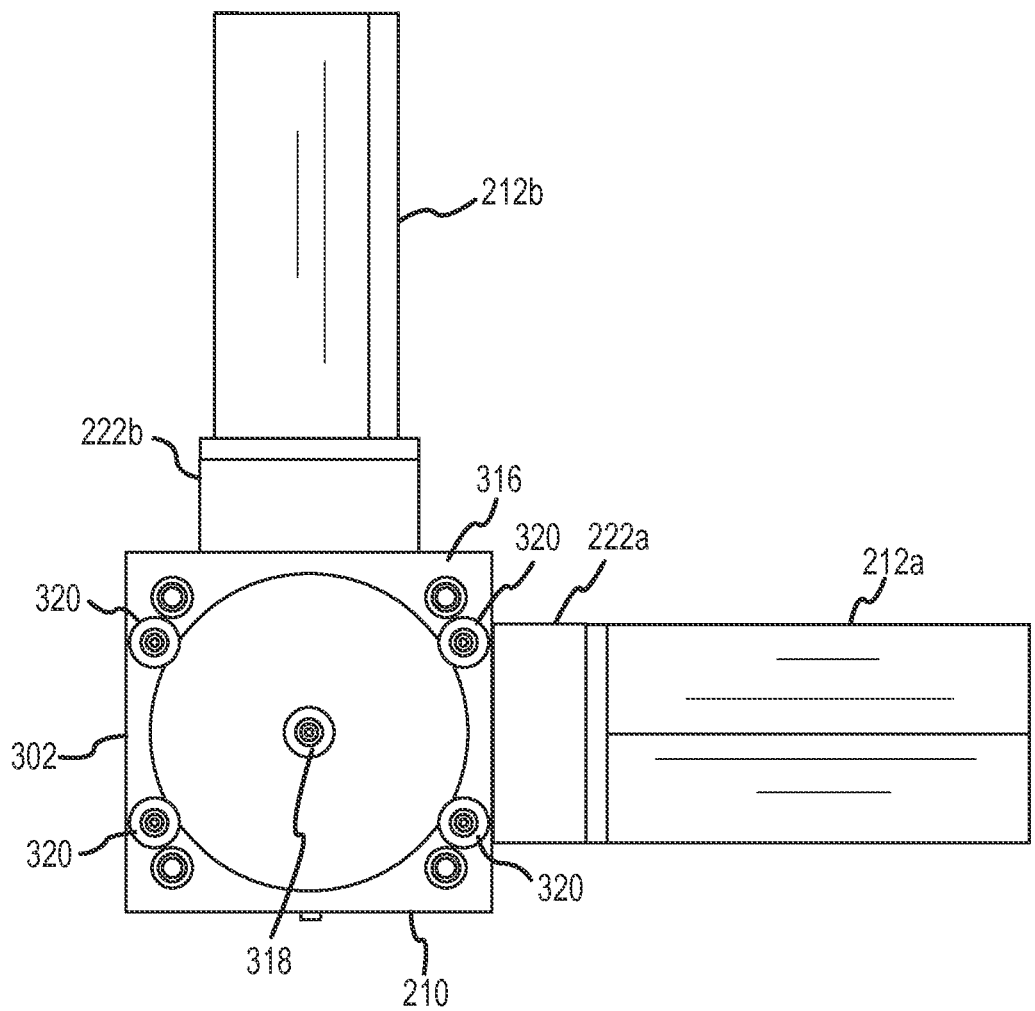
FIG. 15 is a top view of an example light detection assembly including a dichroic mirror unit with a rotatably adjustable dichroic mirror.
Figure 16:
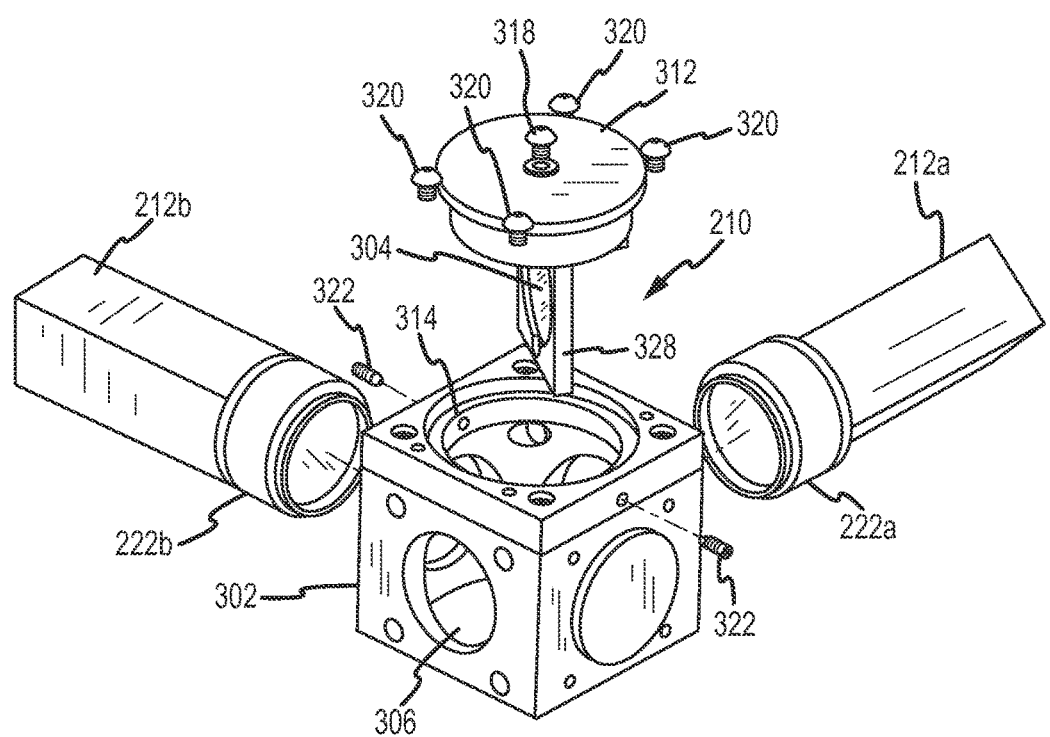
FIG. 16 is an expanded perspective view of the light detection assembly shown in FIG. 15.
Figure 17:
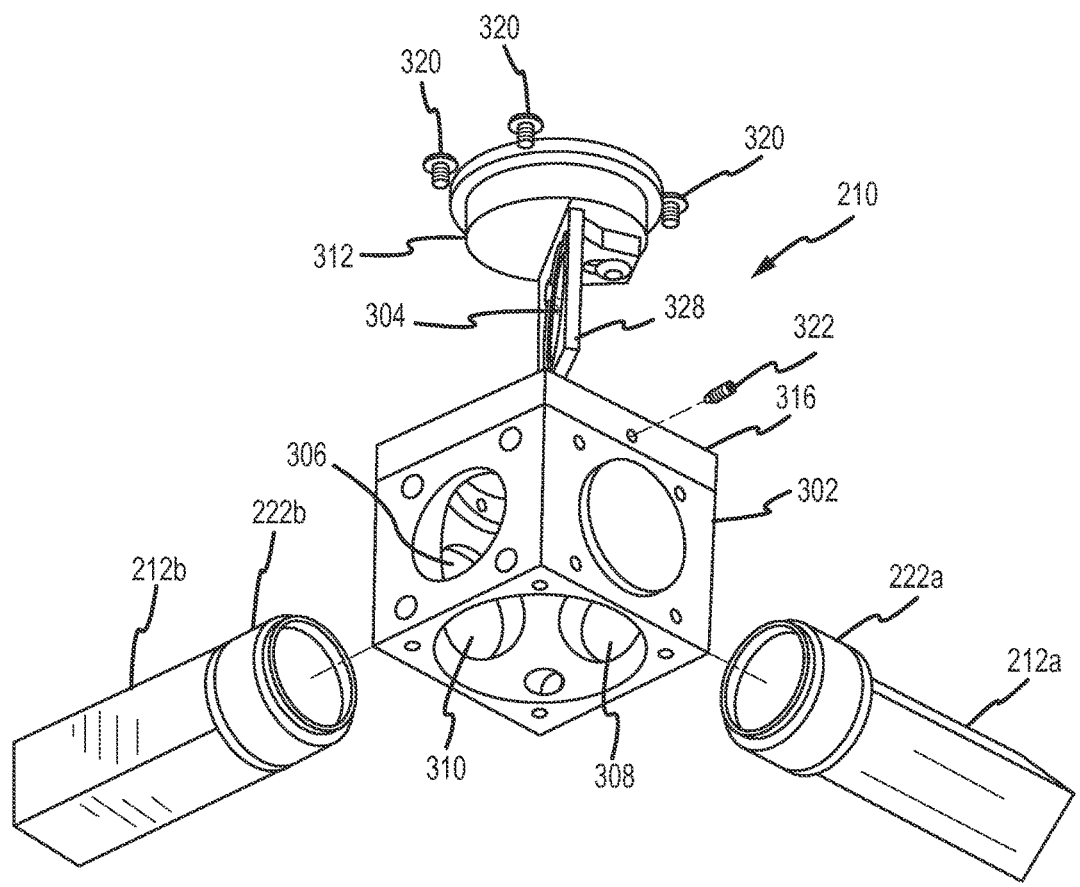
FIG. 17 is another expanded perspective view of the light detection assembly shown in FIG. 15.
Figure 18:
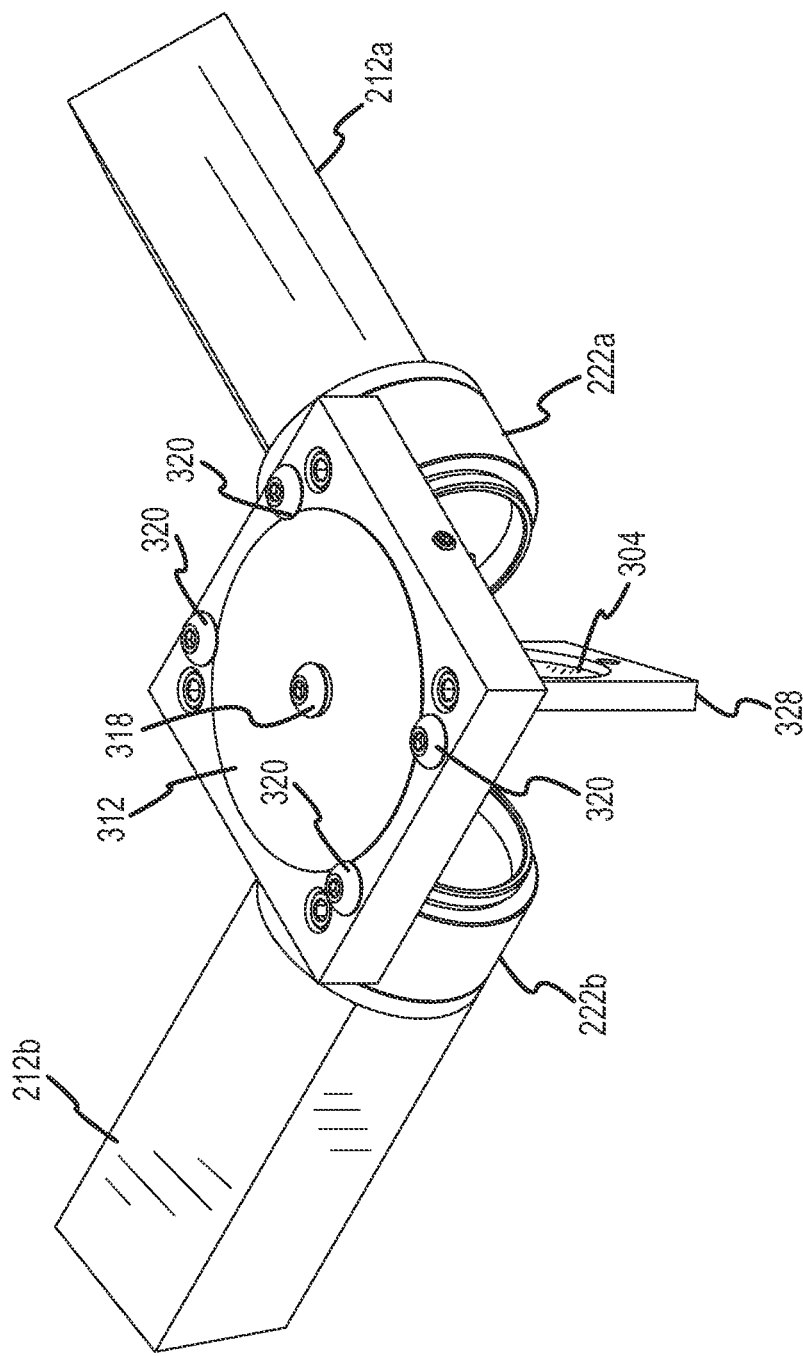
FIG. 18 is a perspective view of a portion of the light detection assembly shown in FIG. 15.
Figure 19:
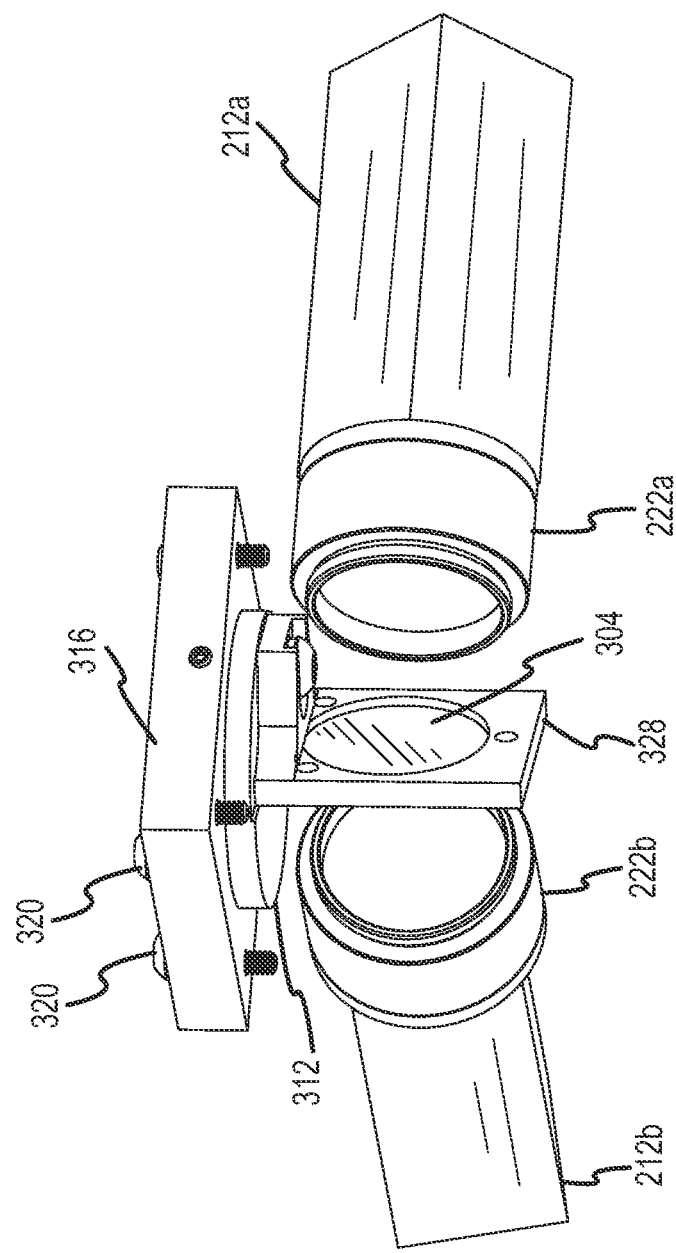
FIG. 19 is another perspective view of the same portion of the light detection assembly shown in FIG. 18.

Reference is now made primarily to FIGS. 15-22 in relation to adjustability of positioning of the dichroic mirror in an example design for the dichroic mirror unit 210 of the internal assembly 180 of FIGS. 3-10. FIGS. 15-17 show the light detection system of FIGS. 3-10 including the dichroic mirror unit 210, light detectors 212 and band-pass filter units 222. The dichroic mirror unit 210 includes a housing 302 in which is disposed a dichroic mirror 304. The housing 302 includes a light inlet port 306 disposed to receive light along the second optical path of the internal assembly 180 and two light outlet ports 308 and 310 disposed to permit light to exit the housing 302 to be received by the band-pass filter units 222 and ultimately by the light detectors 212. The dichroic mirror 304 is disposed in the housing 302 and oriented to receive light entering the housing through the inlet port 306 and to direct different portions of such incident light to the different light detectors 212. A portion of the light passing through the dichroic mirror 304 may pass through the outlet port 308 for detection by the light detector 212a. Another portion of the light may be reflected by the dichroic mirror 304 to pass through the other outlet port 310 to be detected by the other light detector 212b. Light passing through the dichroic mirror 304 will include a first wavelength range of light targeted for detection by the first detector 212a after passing through the corresponding band-pass filter unit 222a, which may include one or more band-pass filters to provide a desired narrow band of light wavelengths to the first light detector 212a. Likewise, a second wavelength range of light, is directed toward the second light detector 212b, with the corresponding band-pass filter unit 222b including one or more band-pass filters to provide a desired narrow band of light wavelengths to the second detector 212b. The dichroic mirror 304 is mounted on a rotatable mount 312, with the dichroic mirror 304 being held by a frame 328. The rotatable mount 312 is rotatable relative to the housing 302 and the light detectors 212 to permit adjustment of the angular positioning, or orientation, of the dichroic mirror 304 relative to the inlet port 306, outlet ports 308 and light detectors 212. The rotatable mount 312 is engaged with and rotatable relative to a mount seat 314 formed in a top 316 of the housing 302. FIGS. 18 and 19 show further detail concerning features of the dichroic mirror unit 210 in relation to orientation with respect to the band-pass filter units 222 and the light detectors 212.

Figure 20:
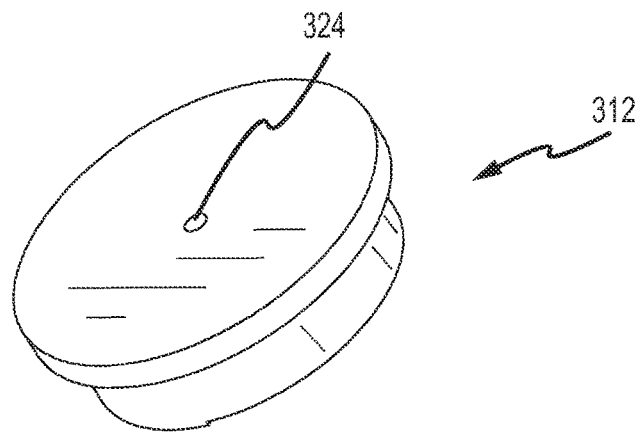
FIGS. 20 and 21 are different perspective views of the rotatable mount of the dichroic mirror unit of the light detection assembly shown in FIG. 15.
Figure 21:
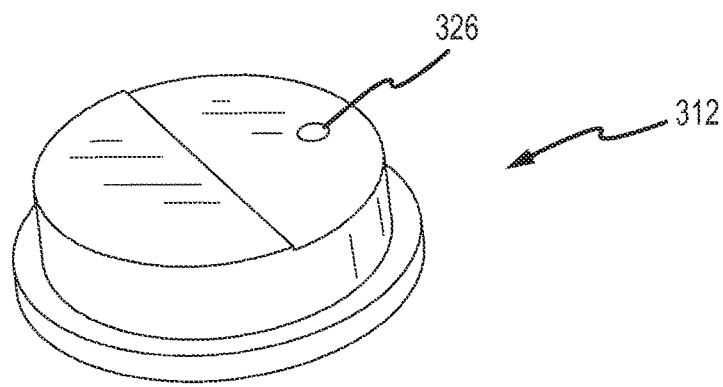
Figure 22:
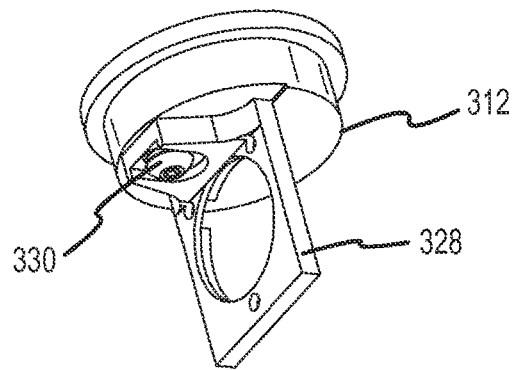
FIG. 22 is a perspective view of the rotatable mount of the dichroic mirror unit of the light detection assembly shown in FIG. 15 on which is mounted a frame for retaining a mounted dichroic mirror.

The dichroic mirror unit 210 includes a locking mechanism that may be changed between a locked configuration and an unlocked configuration to permit or not permit the rotatable mount 312 to be rotated in the mount seat 314 relative to the housing 302. The example locking mechanism that is shown includes four retaining screws 320 that may be screwed down to tightly hold the rotatable mount 312 in a fixed position pressed into the mounting seat 314 with the top of the rotatable mount 312 flush with the top 316 of the housing. The example locking mechanism also includes two set screws 322 that may be advanced to bear on opposing sides of the rotatable mount 312 to further prevent rotation of the rotatable mount 312 relative to the mount seat 314 and to aid locking the rotatable mount 312 in a fixed position to fix the angular positioning of the dichroic mirror 304 relative to the light detectors 312. To unlock the locking mechanism to permit the angular positioning of the dichroic mirror 304 to be changed by rotation of the rotatable mount 312, the set screws 322 may be retracted to a retracted position where the set screws 322 are not in contact with the rotatable mount 312. The retaining screws 320 may also be loosened enough to permit easy rotation of the rotatable mount 312 relative to the housing 302. For example, the rotatable mount 312 may be rotated by rotation of a rotating screw 318 that is firmly secured with the rotatable mount 312, such as using a hex wrench (e.g., Allen wrench) or other appropriate tool that mates with the head of the rotating screw 318. FIGS. 20 and 21 show the rotatable mount 312 and a screw tap 324 on a top side of the rotatable mount 312 that receives the screw 318 and another screw tap 326 on a bottom side of the rotatable mount 312 used to mount the dichroic mirror 304 in the frame 328 to the rotatable mount 312. FIG. 22 depicts the frame 328, which holds the dichroic mirror 304, connected to the bottom side of the rotatable mount 312 by a mounting screw 330 screwed into the screw tap 326 that is shown in FIG. 21.

The design of the dichroic mirror unit 210 that allows adjustment of the angular positioning of the dichroic mirror 304 relative to the light detectors 212 permits convenient servicing to set and reset the angular positioning of the dichroic mirror 304 for enhanced detection of targeted light wavelengths by the light detectors 212 during flow cytometry investigations of sample fluids. The rotatable mount 312 may be unlocked and while the flow cytometer 100 is operating to perform a flow cytometry investigation on a standard fluid containing particles of known composition, an operator or technician may adjust the orientation of the dichroic mirror 304 relative to the light detectors 212 to an identified optimal position based on monitoring output from the light detectors 212 with the dichroic mirror 304 positioned in a variety of different angular positions. The rotatable mount 312 may then be locked down to retain that optimal angular position. A similar process may be followed at a later time during servicing of the flow cytometer 100 to reset to the angular positioning of the dichroic mirror 304 as appropriate to ensure a continued high level of performance of the light detection system.

Not only does the dichroic mirror unit 210 provide a rotatable feature permitting adjustment of the angular positioning of the dichroic mirror 304, but the rotatable feature is provided while also providing that the dichroic mirror 304 is contained in a light-tight enclosure disposed in the enclosure 102 if the flow cytometer 100. The housing 302 is open only to receive light through the light inlet port 306 and to direct light out of the light outlet ports 308 and 310. Those ports mate with light-tight componentry that keeps ambient light from penetrating into the housing 302. Providing such a light-tight enclosure for the dichroic mirror 304 while also providing significant flexibility to easily set and reset the angular positioning of the dichroic mirror 304 provides a significant advantage in the practical utility of the flow cytometer 100.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically compatible, and all such combinations are within the scope of the present disclosure.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, the a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term at "at least a portion" means all or a portion that is less than all. The term "at least a part" means all or a part that is less than all.

What is claimed is:

1. A flow cytometer, comprising:
a light source unit comprising a light source;
a flow cell unit comprising a flow cell with an investigatory flow path to conduct sample fluid flow through the flow cell during operation of the flow cytometer to perform a flow cytometry investigation of sample fluid in the flow cell;
a first optical path between the light source and the flow cell to direct light from the light source to at least a portion of the investigatory flow path;
a light detection system comprising a light detector;
a second optical path between the flow cell and the light detection system to direct at least a portion of light from the investigatory flow path to the light detection system;
an enclosure;
a flow cytometry optical system assembly disposed in the enclosure, the flow cytometry optical system assembly comprising a support platform and flow cytometry optical components supported by the support platform, the flow cytometry optical components comprising the light source unit, flow cell unit and light detector;
a vibration isolation structure, wherein the flow cytometer has an operational configuration in which the flow cytometry optical system assembly within the enclosure is supported by the vibration isolation structure to provide a barrier to propagation of vibrations to the flow cytometry optical system assembly; and
a shear protection structure that is moveable between a first position to protect the vibration isolation structure from damage by shear stresses and a second position to not protect the vibration isolation structure from damage by shear stresses;
and wherein:
in the operational configuration the shear protection structure is in the second position;
the flow cytometer has a shipping configuration in which the shear protection structure is in the first position;
the vibration isolation structure comprises a plurality of vibration isolation mounts supported by and extending above corresponding support members within the enclosure; and
the shear protection structure includes a slidable member that is slidable relative to a said support member between the first position and the second position.

2. A flow cytometer according to claim 1, wherein the vibration isolation structure comprises vibration isolation material that supports the entire weight of the flow cytometry optical system assembly when the flow cytometer is in the operational configuration.

3. A flow cytometer according to claim 2, wherein in the operational configuration, the vibration isolation material that supports the entire weight of the flow cytometry optical system assembly is in compression between the platform and a rigid support structure that supports the vibration isolation material.

4. A flow cytometer according to claim 2, wherein the vibration isolation material has a Shore A durometer hardness in a range of from 20 to 80.

5. A flow cytometer according to claim 4, wherein the support platform is of a material of construction having a hardness of at least 10 Rockwell B.

6. A flow cytometer according to claim 1, wherein the vibration isolation structure is disposed entirely within the enclosure.

7. A flow cytometer according to claim 1, wherein the vibration isolation structure is a first vibration isolation structure and the flow cytometer includes a second vibration isolation structure; and
the enclosure is supported by the second vibration isolation structure when the flow cytometer is in the operational configuration, the second vibration isolation structure providing a vibration propagation barrier to the enclosure and contents within the enclosure and the first vibration isolation structure providing a vibration propagation barrier between the enclosure and the flow cytometry optical system assembly.

8. A flow cytometer according to claim 7, wherein the second vibration isolation structure comprises second vibration isolation material on which the entire weight of the enclosure and contents within the enclosure are supported, the second vibration isolation material having a Shore A durometer hardness in a range of 40 to 100.

9. A flow cytometer according to claim 1, wherein the flow cytometry optical components are retained in the flow cytometry optical system assembly with fixed relative positioning for flow cytometry operation and the flow cytometry optical system assembly is removable from the enclosure as a unit with the flow cytometry optical components retained in the fixed relative positioning.

10. A flow cytometer according to claim 1, wherein the shear protection structure is retainable in the first position to relieve the vibration isolation structure from supporting at least a portion of the weight of the flow cytometry optical system assembly that is supported by the vibration isolation structure when the shear protection structure is in the second position.

11. A flow cytometer according to claim 1, wherein when the shear protection structure is in the first position, the shear protection structure is attachable to the platform to prevent lateral movement between the platform and the vibration isolation structure.

12. A flow cytometer according to claim 1, wherein the slidable member comprises a slidable sleeve in which a portion of the vibration isolation mount extending above the support member is disposed when the shear protection structure is in the first position but not when the shear protection structure is in the second position.

13. A flow cytometer according to claim 1, comprising at least two of the slidable members with each said slidable member corresponding to a different said support member and a different said vibration isolation mount.

14. A flow cytometer according to claim 1, wherein the flow cytometry optical components supported by the support platform comprise a mirror unit including a mirror disposed along the first optical path between the light source and the flow cell, the mirror being adjustable within the mirror unit to adjust orientation of the mirror relative to the light source.

15. A flow cytometer according to claim 14, wherein the flow cytometry optical components supported by the support platform comprise a lens unit with a focusing lens disposed along the first optical path between the mirror and the flow cell to focus light from the light source toward the investigatory flow path.

16. A flow cytometer according to claim 1, wherein the flow cytometry optical components supported by the platform comprise a dichroic mirror unit including a dichroic mirror disposed along the second optical path between the flow cell and the light detector, the dichroic mirror being adjustable within the dichroic mirror unit to adjust orientation of the dichroic mirror relative to the light detector.

17. A flow cytometer according to claim 16, wherein;
the light detector is a first light detector oriented to receive a first wavelength range of light passing through the dichroic mirror; and
the flow cytometry optical components supported by the support platform comprise a second light detector oriented to receive a second wavelength range of light reflected by the dichroic mirror.

18. A flow cytometer according to claim 17, wherein the dichroic mirror is disposed within a housing and the dichroic mirror is mounted on a rotatable mount that is rotatable to adjust angular positioning of the dichroic mirror, and the rotatable mount is engaged with and rotatable relative to a mount seat in the housing.

19. A flow cytometer according to claim 18, wherein the dichroic mirror is in a light-tight enclosure other than being open to receive light along the first optical path from the investigatory flow cell and to direct light to the first and second light detectors.

20. A flow cytometer according to claim 1, wherein:
the vibration isolation material has a Shore A durometer hardness in a range of from 20 to 80
the support platform is of a material of construction having a hardness of at least 10 Rockwell B;
the flow cytometry optical components are retained in the flow cytometry optical system assembly with fixed relative positioning for flow cytometry operation and the flow cytometry optical system assembly is removable from the enclosure as a unit with the flow cytometry optical components retained in the fixed relative positioning;
the vibration isolation structure is a first vibration isolation structure and the flow cytometer includes a second vibration isolation structure;
the enclosure is supported by the second vibration isolation structure when the flow cytometer is in the operational configuration, the second vibration isolation structure providing a vibration propagation barrier to the enclosure and contents within the enclosure and the first vibration isolation structure providing a vibration propagation barrier between the enclosure and the flow cytometry optical system assembly;
the second vibration isolation structure comprises second vibration isolation material on which the entire weight of the enclosure and contents within the enclosure are supported, the second vibration isolation material having a Shore A durometer hardness in a range of 40 to 100;
the flow cytometry optical components supported by the support platform comprise a mirror unit including a mirror disposed along the first optical path between the light source and the flow cell, the mirror being adjustable within the mirror unit to adjust orientation of the mirror relative to the light source;
the flow cytometry optical components supported by the support platform comprise a dichroic mirror unit including a dichroic mirror disposed along the second optical path between the flow cell and the light detector, the dichroic mirror being rotatably adjustable within the dichroic mirror unit to adjust angular positioning of the dichroic mirror relative to the light detector;
the dichroic mirror is disposed within a housing and the dichroic mirror is mounted on a rotatable mount that is rotatable to adjust angular positioning of the dichroic mirror, and the rotatable mount is engaged with and rotatable relative to a mount seat in the housing; and the dichroic mirror is in a light-tight enclosure other than being open to receive light along the first optical path from the investigatory flow cell and to direct light to the first and second light detectors.

\* \* \* \* \*